United States Patent
Zbozien et al.

(10) Patent No.: US 11,246,958 B2
(45) Date of Patent: *Feb. 15, 2022

(54) HAEMOSTATIC COMPOSITIONS

(71) Applicant: HAEMOSTATIX LIMITED, Nottingham (GB)

(72) Inventors: Renata Zbozien, Nottingham (GB); John Benjamin Nichols, Nottingham (GB)

(73) Assignee: HAEMOSTATIX LIMITED, Nottingham (GB)

(*) Notice: Subject to any disclaimer, the term of this patent is extended or adjusted under 35 U.S.C. 154(b) by 0 days.

This patent is subject to a terminal disclaimer.

(21) Appl. No.: 15/572,915

(22) PCT Filed: May 11, 2016

(86) PCT No.: PCT/GB2016/051346
§ 371 (c)(1),
(2) Date: Nov. 9, 2017

(87) PCT Pub. No.: WO2016/181137
PCT Pub. Date: Nov. 17, 2016

(65) Prior Publication Data
US 2018/0154038 A1    Jun. 7, 2018

(30) Foreign Application Priority Data

May 11, 2015   (GB) ..................... 1508024

(51) Int. Cl.
*A61L 26/00* (2006.01)

(52) U.S. Cl.
CPC ....... *A61L 26/0023* (2013.01); *A61L 26/0047* (2013.01); *A61L 26/0052* (2013.01); *A61L 26/0061* (2013.01); *A61L 26/0066* (2013.01); *A61L 2300/418* (2013.01); *A61L 2400/04* (2013.01)

(58) Field of Classification Search
None
See application file for complete search history.

(56) References Cited

U.S. PATENT DOCUMENTS

| | | | |
|---|---|---|---|
| 4,407,829 A | 10/1983 | Sjolander | |
| 8,124,120 B2 * | 2/2012 | Sadozai | A61K 9/0024 424/426 |
| 10,994,047 B2 * | 5/2021 | Zbozien | A61P 17/02 |
| 2003/0032622 A1 * | 2/2003 | Ljungquist | C08B 37/0072 514/54 |
| 2003/0171539 A1 | 9/2003 | Quentin et al. | |
| 2004/0101546 A1 | 5/2004 | Gorman et al. | |
| 2005/0107583 A1 | 5/2005 | Jiang et al. | |
| 2005/0123588 A1 | 6/2005 | Zhu et al. | |
| 2006/0233855 A1 * | 10/2006 | Seliktar | A61L 27/225 424/422 |
| 2009/0203619 A1 * | 8/2009 | Goodall | A61K 47/65 514/13.9 |
| 2010/0249044 A1 | 9/2010 | Walker | |
| 2012/0114682 A1 * | 5/2012 | Barker | C07K 5/1008 424/185.1 |
| 2016/0324977 A1 * | 11/2016 | Zbozien | A61L 26/0028 |

FOREIGN PATENT DOCUMENTS

| | | | | |
|---|---|---|---|---|
| CN | 104398287 A | 3/2015 | | |
| EP | 3020733 A1 | 5/2016 | | |
| GB | 2501348 A | 10/2013 | | |
| RU | 2486921 C2 | 7/2013 | | |
| WO | 92/22312 A1 | 12/1992 | | |
| WO | 00/16801 A1 | 3/2000 | | |
| WO | 2006/005340 A1 | 1/2006 | | |
| WO | 2006/012541 A2 | 2/2006 | | |
| WO | 2010/088469 A2 | 8/2010 | | |
| WO | 2012/104638 A1 | 8/2012 | | |
| WO | WO-2012104638 A1 * | 8/2012 | ............. | A61K 38/08 |
| WO | 2013/053759 A2 | 4/2013 | | |
| WO | WO-2013053759 A2 * | 4/2013 | ............ | A61K 31/765 |
| WO | 2013/060769 A2 | 5/2013 | | |
| WO | 2013/114132 A1 | 8/2013 | | |
| WO | 2015/005345 A1 | 1/2015 | | |
| WO | 2015/104544 A1 | 7/2015 | | |
| WO | WO-2015104544 A1 * | 7/2015 | ......... | A61L 26/0028 |

OTHER PUBLICATIONS

Anonymous. "10ml Cross Linked Hyaluronic Gel Dermal Filler/Hyaluronic Acid Injections For Buttocks" http://www.alibaba.com/product-detail/10ml-Cross-Linked-Hyaluronic-Acid-gel_1963516661.html (Year: 2019).*
Kim et al. "Tissue response to implants of hyaluronic acid hydrogel prepared by microbeads" Tissue Eng. Regen. Med. 11:32-38 ( Year: 2014).*
Darmady et al. "Sterilization by dry heat" J. Clin. Path. 14:38-44 (Year: 1961).*
Sadler and Tam "Peptide Dendrimers: applications and synthesis" Reviews in Molecular Biotechnology 90:195-229. (Year: 2002).*
International Search Report and Written Opinion for PCT/GB2016/051346 (dated Aug. 1, 2016).

(Continued)

*Primary Examiner* — Sudhakar Katakam
*Assistant Examiner* — Zachary J Miknis
(74) *Attorney, Agent, or Firm* — Troutman Pepper Hamilton Sanders LLP (Rochester)

(57) ABSTRACT

A sterile, ready-to-use, flowable haemostatic composition comprises a soluble haemostatic agent comprising a plurality of carriers and a plurality of fibrinogen binding peptides immobilised to the carrier; a biocompatible liquid; and particles of biocompatible cross-linked polysaccharide suitable for use in haemostasis and which are insoluble in the biocompatible liquid. Such compositions may be used for the control of bleeding, especially in surgical procedures.

17 Claims, 11 Drawing Sheets

Specification includes a Sequence Listing.

(56) References Cited

OTHER PUBLICATIONS

PCT International Preliminary Report on Patentability corresponding to PCT/GB2016/051346, dated Nov. 14, 2017.
Sadler et al., "Peptide Dendrimers: Applications and Synthesis," J. Biotechnol. 90(3-4):195-229 (2002).
Miekka et al., "Inactivation of Viral and Prion Pathogens by Gamma-Irradiation under Conditions that Maintain the Integrity of Human Albumin," Vox Sang. 84(1):36-44 (2003).

* cited by examiner

A)

B) Clinically Acceptable Haemostasis

| No Bleeding | Ooze | Very Mild | Mild | Moderate | Severe |
| --- | --- | --- | --- | --- | --- |
| 0 | 1 | 2 | 3 | 4 | 5 |

E)

```
                        SEQUENCE LISTING

<160> NUMBER OF SEQ ID NOS: 17

<210> SEQ ID NO 1
<211> LENGTH: 4
<212> TYPE: PRT
<213> ORGANISM: Homo sapiens

<400> SEQUENCE: 1

Gly Pro Arg Pro
1

<210> SEQ ID NO 2
<211> LENGTH: 4
<212> TYPE: PRT
<213> ORGANISM: Homo sapiens

<400> SEQUENCE: 2

Gly Pro Arg Val
1

<210> SEQ ID NO 3
<211> LENGTH: 7
<212> TYPE: PRT
<213> ORGANISM: Homo sapiens

<400> SEQUENCE: 3

Gly Pro Arg Pro Phe Pro Ala
1               5

<210> SEQ ID NO 4
<211> LENGTH: 7
<212> TYPE: PRT
<213> ORGANISM: Homo sapiens

<400> SEQUENCE: 4

Gly Pro Arg Val Val Ala Ala
1               5

<210> SEQ ID NO 5
<211> LENGTH: 8
<212> TYPE: PRT
<213> ORGANISM: Homo sapiens

<400> SEQUENCE: 5

Gly Pro Arg Pro Val Val Glu Arg
1               5
```

```
<210> SEQ ID NO 6
<211> LENGTH: 6
<212> TYPE: PRT
<213> ORGANISM: Homo sapiens

<400> SEQUENCE: 6

Gly Pro Arg Pro Ala Ala
1               5

<210> SEQ ID NO 7
<211> LENGTH: 7
<212> TYPE: PRT
<213> ORGANISM: Homo sapiens

<400> SEQUENCE: 7

Gly Pro Arg Pro Pro Glu Cys
1               5

<210> SEQ ID NO 8
<211> LENGTH: 7
<212> TYPE: PRT
<213> ORGANISM: Homo sapiens

<400> SEQUENCE: 8

Gly Pro Arg Pro Pro Glu Arg
1               5

<210> SEQ ID NO 9
<211> LENGTH: 6
<212> TYPE: PRT
<213> ORGANISM: Homo sapiens

<400> SEQUENCE: 9

Gly Pro Ser Pro Ala Ala
1               5

<210> SEQ ID NO 10
<211> LENGTH: 4
<212> TYPE: PRT
<213> ORGANISM: Homo sapiens

<400> SEQUENCE: 10

Gly His Arg Pro
1

<210> SEQ ID NO 11
<211> LENGTH: 5
<212> TYPE: PRT
<213> ORGANISM: Homo sapiens

<400> SEQUENCE: 11

Gly His Arg Pro Tyr
1               5

<210> SEQ ID NO 12
<211> LENGTH: 5
<212> TYPE: PRT
<213> ORGANISM: Homo sapiens

<400> SEQUENCE: 12

Gly His Arg Pro Leu
1               5
```

```
<210> SEQ ID NO 13
<211> LENGTH: 5
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Carboxy-terminal end comprises an amide group

<400> SEQUENCE: 13

Gly His Arg Pro Tyr
1               5

<210> SEQ ID NO 14
<211> LENGTH: 7
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: Carboxy-terminal end may comprise an amide
      group

<400> SEQUENCE: 14

Ala Pro Phe Pro Arg Pro Gly
1               5

<210> SEQ ID NO 15
<211> LENGTH: 4
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Pro or His
<220> FEATURE:
<221> NAME/KEY: MISC_FEATURE
<222> LOCATION: (4)..(4)
<223> OTHER INFORMATION: Any amino acid

<400> SEQUENCE: 15

Gly Xaa Arg Xaa

<210> SEQ ID NO 16
<211> LENGTH: 5
<212> TYPE: PRT
<213> ORGANISM: Homo sapiens
<220> FEATURE:
<221> NAME/KEY: misc_feature
<222> LOCATION: (5)..(5)
<223> OTHER INFORMATION: Carboxy-terminal end comprises an amide group

<400> SEQUENCE: 16

Tyr Pro Arg His Gly
1               5

<210> SEQ ID NO 17
<211> LENGTH: 5
<212> TYPE: PRT
<213> ORGANISM: Homo sapiens

<400> SEQUENCE: 17

Gly Pro Arg Pro Gly
1               5
```

HAEMOSTATIC COMPOSITIONS

This application is a national stage application under 35 U.S.C. § 371 of PCT Application No. PCT/GB2016/051346, filed May 11, 2016, which claims priority benefit of Great Britain Application No. 1508024.5, filed May 11, 2015, each of which is hereby incorporated by reference in its entirety.

This invention relates to haemostatic compositions, in particular flowable haemostatic compositions in sterile, ready-to-use form, to methods of producing the haemostatic compositions, and to use of the compositions for the control of bleeding, especially in surgical procedures.

Formation of insoluble fibrin polymer from its soluble precursor fibrinogen is the final stage of blood clotting. Conversion of fibrinogen to fibrin occurs in three steps: limited proteolysis of fibrinogen to fibrin monomer by thrombin; assembly of fibrin monomers into half-staggered, double-stranded protofibrils; and cross-linking of assembled fibrin to strengthen the clot.

The fibrinogen molecule consists of three pairs of non-identical polypeptide chains, Aα, Bβ and γ, linked together by disulfide bonds. Fibrinogen chains are folded into three distinct structural regions, two distal D regions linked to one central E region. Each D region contains polymerization 'a' and 'b' holes located in the C terminus of the γ and Bβ chains, respectively. Thrombin catalyses the removal of short peptides, fibrinopeptides A (FpA) and B (FpB), from the amino-terminus of the Aα and Bβ chains of fibrinogen in the central E region, respectively, exposing two polymerisation sites: "knob A", with amino-terminal sequence Gly-Pro-Arg-; and "knob B", with amino-terminal sequence Gly-His-Arg-. The newly exposed polymerization knobs of one fibrin monomer interact with corresponding holes of another fibrin monomer through 'A-a' and 'B-b' knob-hole interactions, resulting in the assembly of fibrin monomers into half-staggered, double-stranded protofibrils.

The protofibrils aggregate laterally to make thicker fibres that coalesce to form a three-dimensional network of fibrin clot. FpA is cleaved from fibrinogen more rapidly than FpB. Removal of FpA triggers formation of protofibrils, while removal of FpB coincides with their lateral aggregation. FpB release, which is very slow at the start of the reaction, is accelerated upon polymer formation. This delay in FpB cleavage is necessary for normal fibrin assembly, and is also connected with the formation of different types of clots. Fibrin I, in which only the FpAs are removed, is less compact and is more readily digested by plasmin, whereas fibrin II, in which both FpA and FpB are removed, is more compact and more resistant to fibrinolysis.

Studies with snake venom enzymes that remove only FpA or principally FpB have demonstrated that fibrin clots can be formed by either 'A-a' or 'B-b' interactions, indicating that both interactions can mediate protofibril formation. Experiments with a variant recombinant fibrinogen showed that 'B-b' interactions may play a substantial role in protofibril formation when 'A-a' interactions are weakened. Other studies have demonstrated that only 'A-a' interactions occur during the binding of fibrin fragments to fibrinogen molecules even when both 'B' knobs and 'b' holes are available, and that 'B-b' knob-hole interactions were apparent only when 'A-a' interactions were excluded. However, peptide inhibition studies have indicated that 'B-b' interactions can occur simultaneously with 'A-a'.

Fibrin is stabilised by the formation of covalent cross-links between the side chains of different molecules in the fibrin fibre. Peptide bonds are formed between specific glutamine and lysine side chains in a transamidation reaction that is catalysed by Factor XIIIa.

Application of direct pressure at a bleeding site may not be sufficient to control bleeding when the source of bleeding is hard to identify (for example, in diffuse venous bleeding), or when an inherent coagulopathy is present. Haemostasis is also compromised due to the presence of antiplatelet and anticoagulation agents, especially in patients undergoing cardiac or vascular surgery, as well as from changes associated with cardiopulmonary bypass. In such cases topical haemostatic agents provide useful adjuncts to the conventional methods of achieving haemostasis.

Gelatin-based haemostats are used in surgical procedures. Gelatin powder, when mixed with fluid, can be prepared in various forms depending on the end use, and the ratio of fluid to powder. For example, where higher concentrations of fluid are employed, a paste or slurry that is useful as a flowable haemostat may be prepared for use in diffuse bleeding, particularly from uneven surfaces or hard-to-reach areas. Such pastes are prepared at the point of use by mechanical agitation and mixing of the powder and liquid to provide uniformity of the composition. The paste then is placed into a delivery means or applicator, for example, a syringe, and applied to the wound.

Some gelatin-based haemostats are available commercially in kit form as a flowable gelatin matrix, with lyophilized thrombin. Prior to use, the lyophilized thrombin is reconstituted in water or saline, and mixed with the gelatin matrix. The granular nature of the gelatin matrix enables the material to conform to any irregular wound geometries. The components of the mixture act synergistically to promote haemostasis at the bleeding site. The gelatin granules swell upon exposure to blood, reducing blood flow, and providing gentle tamponade. Blood passing through the spaces between the granules is exposed to high concentrations of thrombin. Thrombin enzymatically converts fibrinogen in the blood into fibrin monomers, which polymerize. The fibrin polymer entraps the gelatin granules and other cellular elements at the bleeding site. The body resorbs the gelatin granules incorporated in the resulting clot within several weeks, consistent with the time-course of normal wound healing.

One commercially available gelatin-based haemostatic kit is FLOSEAL Hemostatic Matrix kit. The gelatin matrix consists of cross-linked gelatin granules, provided as a sterile gel in a disposable syringe. The thrombin is supplied as a sterile freeze-dried powder preparation, and is provided with sterile sodium chloride as a diluent. The gelatin matrix is made by extraction of collagen from bovine corium followed by gelatinization of the collagen, cross-linking with glutaraldehyde, and grinding of the cross-linked gelatin to 500-600 μm sized particles. Another commercially available kit is SURGIFLO Hemostatic Matrix Kit—with Thrombin. The matrix is supplied in a prefilled syringe to be mixed with thrombin. The gelatin used to make the matrix is derived from pig skins. The gelatin is processed to yield a gelatin powder product, which is then processed to yield a paste. The thrombin is provided as a lyophilized powder for reconstitution in water.

Whilst haemostatic agents comprising gelatin matrix and thrombin are effective in controlling bleeding during surgery, products of this type have several disadvantages. In particular, thrombin is not stable in solution, and cannot be sterilized in solution without destroying at least some of its activity. Consequently, thrombin is provided separately as a lyophilized powder for reconstitution, before mixing with the gelatin matrix within a few hours prior to use. These steps risk compromising the sterility of the mixture, are inconvenient for surgical procedures, and make the products unviable for treatment of traumatic wounds outside a hospital. Thrombin provided in current commercially available kits is prepared from pooled human plasma, obtained from licensed plasma collection centres, through a series of separation and filtration steps. Whilst these procedures significantly reduce the risk of viral or prion infection, they do not eliminate risk.

There is a need, therefore, to provide stable, ready-to-use, haemostatic agents suitable for controlling bleeding in surgical procedures. There is also a need to provide ready-to-use, haemostatic agents that are more resistant to sterilization than conventional flowable haemostatic agents comprising thrombin. A further need is for haemostatic agents that have even further reduced risk of viral or prion infectivity than current commercially available flowable haemostatic agents comprising thrombin.

According to the invention there is provided a haemostatic composition comprising: a soluble haemostatic agent comprising a plurality of carriers and a plurality of fibrinogen-binding peptides immobilised to each carrier; a biocompatible liquid; and particles of a biocompatible cross-linked polysaccharide suitable for use in haemostasis and which are insoluble in the biocompatible liquid.

According to certain embodiments of the invention, the compositions are ready-to-use, flowable, haemostatic compositions.

It has been found that the haemostatic agents in compositions of the invention are surprisingly resistant to sterilization, particularly steam sterilization, or dry-heat sterilization. Consequently, compositions of the invention may be sterilized using conventional sterilization methods without significant loss of haemostatic activity. This is an important advantage because it allows the compositions to be provided as hydrated, sterile, ready-to-use, flowable haemostatic compositions. Conventional gelatin-based haemostats comprising thrombin are not stable when heat or steam sterilised in hydrated, ready-to-use form.

The term "haemostatic" is used herein to mean the ability to stop or minimize bleeding.

The term "biocompatible" is used herein to mean that the material is compatible with living tissue by not being toxic or injurious and not causing immunological rejection. The material should preferably meet the criteria in standard #ISO 10993-1 promulgated by the International Organization for Standardization (NAMSA, Northwood, Ohio).

The term "flowable" is used herein to mean that the compositions flow when subjected to stresses above a threshold level, for example when extruded through an orifice or cannula or when packed into a delivery site using a spatula. The threshold stresses are typically in the range from $3 \times 10^4$ Pa to $5 \times 10^5$ Pa. The compositions, however, will remain generally immobile when subjected to stresses below the threshold level. A flowable composition is generally able to conform to irregular wound geometries at a target site to which the composition is delivered.

The haemostatic agent, liquid and insoluble particles may be combined and mixed under conditions effective to provide a substantially homogeneous haemostatic composition comprising a continuous, biocompatible liquid phase, comprising the particles substantially homogenously dispersed throughout the liquid phase.

As used herein, "substantially homogenous" denotes that physical state of the compositions in which the solid particles are uniformly dispersed throughout the continuous liquid phase such that the ratio of solid:liquid and the density of any portion or cross-section of the composition are substantially the same.

According to certain aspects of the invention, the compositions are resorbable. The term "resorbable" is used herein to mean that the compositions will degrade or solubilize, when administered directly to a target site of a patient's body (and not protected within an implant device such as a breast implant), over a time period of one year or less, usually from 1 day to 1 year, more usually from 1 to 120 days, or from 1 to 90 days, or from 2 to 30 days, following their initial application. A protocol for measuring resorption and degradation is set out in WO 98/08550.

The haemostatic agent used in compositions of the invention comprises a plurality of carriers and a plurality of fibrinogen-binding peptides immobilised to each carrier. It has surprisingly been found that the haemostatic agent is able to polymerise fibrinogen when present in a haemostatic composition of the invention.

A haemostatic agent for use in compositions of the invention is able to polymerise fibrinogen, in the absence of thrombin, in aqueous solution. Each fibrinogen molecule can bind at least two of the fibrinogen-binding peptides. Because a plurality of fibrinogen-binding peptides are immobilised to each carrier, the fibrinogen molecules become linked together via the carriers. Non-covalent bonds are formed between the fibrinogen molecules and the fibrinogen-binding peptides. In aqueous solution, a hydrogel comprising polymerised fibrinogen is formed when the haemostatic agent is contacted with fibrinogen.

The haemostatic agent should be soluble in the biocompatible liquid, and in blood plasma. The haemostatic agent may have a solubility of at least 10 mg per ml of solvent, for example 10-1000 mg/ml, 33-1000 mg/ml, or 33-100 mg/ml. The haemostatic agent should be suitable for administration to a bleeding wound site. The carriers may comprise a polymer, for example a protein, a polysaccharide, or a synthetic biocompatible polymer, such as polyethylene glycol, or a combination of any of these. Albumin is an example of a protein carrier. In preferred embodiments, the fibrinogen-binding peptides are covalently immobilised to the carriers.

In some embodiments, the soluble haemostatic agent is a soluble agent for formation of a biogel as described in WO 2008/065388 (the contents of which are incorporated herein in their entirety). WO 2008/065388 describes formation of a biogel using an agent that comprises several fibrinogen-binding peptides (each comprising the fibrinogen-binding peptide sequence GPRP- at the amino-terminal end of the peptide) conjugated to a soluble human serum albumin (HSA) carrier.

In some embodiments of the invention, each carrier of the haemostatic agent comprises a branched core, and a plurality of fibrinogen-binding peptides separately covalently attached to each branched core. For example, the haemostatic agent may be a peptide dendrimer comprising a branched core, and a plurality of fibrinogen-binding peptides separately covalently attached to the branched core.

The branched core may comprise:
from two to ten multi-functional amino acid residues, wherein each fibrinogen-binding peptide is separately covalently attached to a multi-functional amino acid residue of the branched core;
a plurality of multi-functional amino acid residues, wherein one or more fibrinogen-binding peptides are separately covalently attached to each of at least two adjacent multi-functional amino acid residues of the branched core;

a plurality of multi-functional amino acid residues, wherein two or more fibrinogen-binding peptides are separately covalently attached to at least one of the multi-functional amino acid residues of the branched core;

a plurality of multi-functional amino acid residues, wherein two or more multi-functional amino acid residues are covalently linked through a side chain of an adjacent multi-functional amino acid residue; or a single multi-functional amino acid residue, and a fibrinogen-binding peptide is separately covalently attached to each functional group of the multi-functional amino acid residue;

wherein the multi-functional amino acid residues comprise tri- or tetra-functional amino acid residues, or tri- and tetra-functional amino acid residues, or the single multi-functional amino acid residue is a tri- or tetra-functional amino acid residue.

Each fibrinogen-binding peptide has a different point of attachment to the branched core, so the fibrinogen-binding peptides are referred to herein as being "separately covalently attached" to the branched core.

The branched core comprises any suitable amino acid sequence. The branched core may comprise up to ten multi-functional amino acid residues, for example two to ten, or two to six multi-functional amino acid residues.

The branched core may comprise a plurality of consecutive multi-functional amino acid residues. The branched core may comprise up to ten consecutive multi-functional amino acid residues.

The term "tri-functional amino acid" is used herein to refer to any organic compound with a first functional group that is an amine ($-NH_2$), a second functional group that is a carboxylic acid ($-COOH$), and a third functional group. The term "tetra-functional amino acid" is used herein to refer to any organic compound with a first functional group that is an amine ($-NH_2$), a second functional group that is a carboxylic acid ($-COOH$), a third functional group, and a fourth functional group. The third and fourth functional group may be any functional group that is capable of reaction with a carboxy-terminal end of a fibrinogen-binding peptide, or with a functional group of a linker attached to the carboxy-terminal end of a fibrinogen-binding peptide.

Multifunctional amino acids may comprise a central carbon atom (α- or 2-) bearing an amino group, a carboxyl group, and a side chain bearing a further functional group (thereby providing a tri-functional amino acid), or a further two functional groups (thereby providing a tetra-functional amino acid.

The, or each, multi-functional amino acid residue may be a residue of a proteinogenic or non-proteinogenic multi-functional amino acid, or a residue of a natural or unnatural multi-functional amino acid.

Proteinogenic tri-functional amino acids possess a central carbon atom (α- or 2-) bearing an amino group, a carboxyl group, a side chain and an α-hydrogen levo conformation. Examples of suitable tri-functional proteinogenic amino acids include L-lysine, L-arginine, L-aspartic acid, L-glutamic acid, L-asparagine, L-glutamine, and L-cysteine.

Examples of suitable tri-functional non-proteinogenic amino acid residues include D-lysine, beta-Lysine, L-ornithine, D-ornithine, and D-arginine residues.

Thus, examples of suitable tri-functional amino acid residues for use in the haemostatic agent of compositions of the invention include lysine, ornithine, arginine, aspartic acid, glutamic acid, asparagine, glutamine, and cysteine residues, such as L-lysine, D-lysine, beta-Lysine, L-ornithine, D-ornithine, L-arginine, D-arginine, L-aspartic acid, D-aspartic acid, L-glutamic acid, D-glutamic acid, L-asparagine, D-asparagine, L-glutamine, D-glutamine, L-cysteine, and D-cysteine residues.

Examples of suitable multi-functional unnatural amino acids suitable for use in the haemostatic agent of compositions of the invention include Citrulline, 2,4-diaminoisobutyric acid, 2,2'-diaminopimelic acid, 2,3-diaminopropionic acid, and cis-4-amino-L-proline. Multi-functional unnatural amino acids are available from Sigma-Aldrich.

In some embodiments, the branched core may comprise a homopolymeric multi-functional amino acid sequence, for example a poly-lysine, poly-arginine, or poly-ornithine sequence, such as a branched core comprising from two to ten, or from two to six, consecutive lysine, arginine, or ornithine residues. In other embodiments, the branched core may comprise different multi-functional amino acid residues, for example one or more lysine residues, one or more arginine residues, and/or one or more ornithine residues.

In other embodiments, the branched core may comprise a plurality of multi-functional amino acid residues, and one or more other amino acid residues.

Where the branched core comprises a plurality of multi-functional amino acid residues, adjacent multi-functional amino acid residues may be linked together by amino acid side chain links, by peptide bonds, or some adjacent multi-functional amino acid residues may be linked together by side chain links and others by peptide bonds.

In further embodiments, the branched core may comprise two or more multi-functional amino acid residues, and at least one fibrinogen-binding peptide is separately attached to each of two or more of the multi-functional amino acid residues, and two or more fibrinogen-binding peptides are separately attached to at least one of the multi-functional amino acid residues of the branched core.

According to other embodiments, two fibrinogen-binding peptides are separately attached to a terminal multi-functional amino acid residue of the branched core.

Examples of structures of peptide dendrimers suitable for use as haemostatic agents in compositions of the invention include peptide dendrimers in which:

the branched core comprises a first tri-functional amino acid residue to which two fibrinogen-binding peptides are attached, and a second tri-functional amino acid residue to which one fibrinogen-binding peptide is attached;

the branched core comprises a first tri-functional amino acid residue to which two fibrinogen-binding peptides are attached, and a second tri-functional amino acid residue to which two fibrinogen-binding peptides are attached;

the branched core comprises a first tri-functional amino acid residue to which two fibrinogen-binding peptides are attached, a second tri-functional amino acid residue to which one fibrinogen-binding peptide is attached, and a third tri-functional amino acid residue to which one fibrinogen-binding peptide is attached; or the branched core comprises a first tri-functional amino acid residue to which two fibrinogen-binding peptides are attached, a second tri-functional amino acid residue to which one fibrinogen-binding peptide is attached, a third tri-functional amino acid residue to which one fibrinogen-binding peptide is attached, and a fourth tri-functional amino acid residue to which one fibrinogen-binding peptide is attached.

A peptide dendrimer suitable for use as a haemostatic agent in a composition of the invention may comprise the following general formula (I):

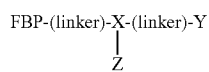
(I)

where:
FBP is a fibrinogen-binding peptide;
-(linker)- is an optional linker, preferably a non-peptide linker;
X is a tri-functional amino acid residue, preferably lysine, ornithine, or arginine;
Y is —FBP, or —NH$_2$;
Z is -(linker)-FBP when Y is —FBP, or -[—X$_n$-(linker)-FBP]$_a$-(linker)-FBP when Y is —NH$_2$;
where:
X$_n$ is a tri-functional amino acid residue, preferably lysine, L-ornithine, or arginine; and
a is 1-10, preferably 1-3.

For example, when Y is NH$_2$, Z is -[—X$_n$-(linker)-FBP]$_a$-(linker)-FBP, the structure of the dendrimer is as follows:
where a is 1:

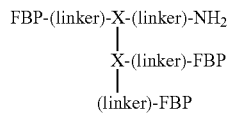

or, where a is 2:

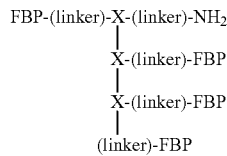

or, where a is 3:

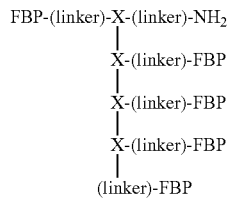

Alternatively, Z is -[—X$_n$-(linker)-FBP]$_a$-(linker)-FBP when Y is —FBP;
where:
X$_n$ is a tri-functional amino acid residue, preferably lysine, L-ornithine, or arginine; and
a is 1-10, preferably 1-3.

For example, when Y is —FBP, Z is -[—X$_n$-(linker)-FBP]$_a$-(linker)-FBP and a is 1, the structure of the dendrimer is as follows:

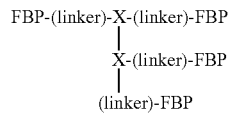

A peptide dendrimer suitable for use as a haemostatic agent in a composition of the invention of the invention may comprise the following general formula (II):

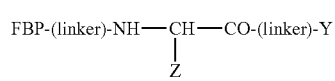
(II)

where:
FBP is a fibrinogen-binding peptide;
-(linker)- is an optional linker, preferably comprising —NH(CH$_2$)$_5$CO—;
Y is —FBP, or —NH$_2$;
Z is:
—R-(linker)-FBP, when Y is —FBP, or

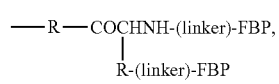

when Y is —NH$_2$; or

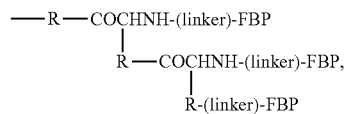

when Y is —NH$_2$; or

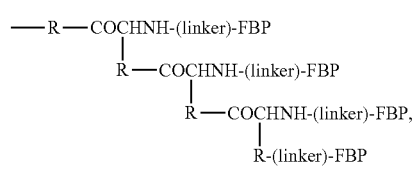

when Y is —NH$_2$;
where R is —(CH$_2$)$_4$NH—, —(CH$_2$)$_3$NH—, or —(CH$_2$)$_3$NHCNHNH—.

Consequently, in one embodiment, Z may be:

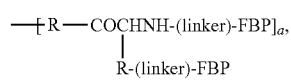

when Y is —NH$_2$;
where R is —(CH$_2$)$_4$NH—, —(CH$_2$)$_3$NH—, or —(CH$_2$)$_3$NHCNHNH—;
where a is 1-3.
Alternatively, a may be 4-10, or it may be 1-10.

In another embodiment, Z is:

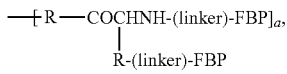

when Y is —FBP;
where R is —(CH$_2$)$_4$NH—, —(CH$_2$)$_3$NH—, or —(CH$_2$)$_3$NHCNHNH—;
where a is 1-10, preferably 1-3.
For example, Z is:

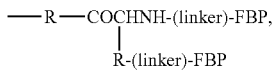

when Y is —FBP and a is 1.

A peptide dendrimer suitable for use as a haemostatic agent in a composition of the invention may comprise the following general formula (III):

$$\text{FBP-(linker)-NH} - \underset{\underset{Z}{|}}{\text{CH}} - \text{CO-(linker)-Y} \qquad (III)$$

where:
FBP is a fibrinogen-binding peptide;
-(linker)- is an optional linker, preferably comprising —NH(CH$_2$)$_5$CO—;
Y is —FBP, or —NH$_2$;
Z is:
—(CH$_2$)$_4$NH-(linker)-FBP, when Y is —FBP; or

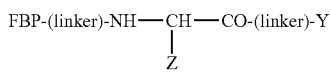

when Y is —NH$_2$; or

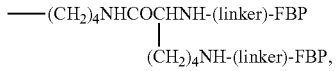

when Y is —NH$_2$; or

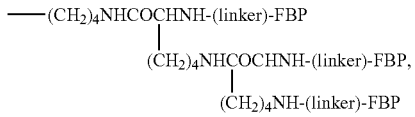

when Y is —NH$_2$.

Consequently, in one embodiment, Z may be:

when Y is —NH$_2$;
where a is 1-3.
Alternatively a is 4-10, or it may be 1-10.
In another embodiment, Z is:

when Y is —FBP;
where a is 1-10, preferably 1-3.
For example, Z is:

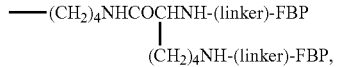

when Y is —FBP and a is 1.

Any suitable fibrinogen-binding peptide (FBP) may be used in a haemostatic agent in a composition of the invention. For example, a FBP may be capable of binding to a region of fibrinogen that is naturally bound to fibrin or by the platelet membrane glycoproteins GPIIb-IIIa. Fibrin binding to fibrinogen is discussed in Mosesson et al. 2001, *Ann. N.Y. Acad. Sci.*, 936, 11-30. Binding of GPIIb-IIIa to fibrinogen is discussed in Bennett, 2001, *Annals of NY Acad. Sci.*, 936, 340-354.

The term "peptide" as used herein also incorporates peptide analogues. Several peptide analogues are known to the skilled person. Any suitable analogue may be used provided fibrinogen is able to bind the fibrinogen binding peptide.

Examples of suitable fibrinogen binding peptides and how they may be identified are provided in WO 2005/035002, WO 2007/015107 and WO 2008/065388.

Examples of sequences of suitable FBPs include: GPR-; GPRP- (SEQ ID NO: 1); GPRV- (SEQ ID NO: 2); GPRPFPA- (SEQ ID NO: 3); GPRVVAA- (SEQ ID NO: 4); GPRPVVER- (SEQ ID NO: 5); GPRPAA- (SEQ ID NO: 6); GPRPPEC- (SEQ ID NO: 7); GPRPPER- (SEQ ID NO: 8); GPSPAA- (SEQ ID NO: 9); GHR-, GHRP- (SEQ ID NO: 10), GHRPY- (SEQ ID NO: 11), GHRPL- (SEQ ID NO: 12), GHRPY amide- (SEQ ID NO: 13); APFPRPG (SEQ ID NO: 14).

A preferred example of a FBP comprises the amino acid sequence G(P,H)RX- (SEQ ID NO: 15) at its amino terminal end, where X is any amino acid, and (P,H) means that either proline or histidine is present at that position.

The FBPs attached to a carrier may comprise the same, or different sequence. The FBPs may each be 3-60, 3-30, or 3-10, amino acid residues in length.

In some embodiments, each fibrinogen-binding peptide binds to fibrinogen with a dissociation constant ($K_D$) of between $10^{-9}$ to $10^{-6}$ M, for example around 10, 20, 30, 40, 50, 60, 70, 80, 90, 100, 110, 120, 130, 140, 150, 200, 250, 300, 350, 400, or more nM. A $K_D$ of around 100 nM is preferred. The dissociation constant can be measured at equilibrium. For example, radio-labelled fibrinogen of known concentration can be incubated with microspheres to

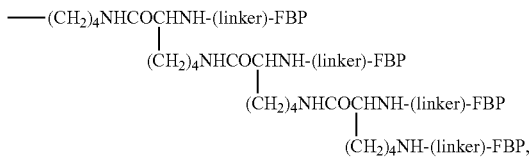

which the fibrinogen binding moiety has been cross-linked. Typically 5 μM peptide is cross-linked to 1 gm microspheres, or 15-40 μmoles of peptide is cross-linked to 1 gm of microspheres. The peptide-linked microspheres are diluted to 0.5 mg/ml, and incubated in isotonic buffer at pH 7.4 (for example 0.01M Hepes buffer containing 0.15M NaCl) with radio labelled fibrinogen at concentrations of between 0.05 and 0.5 mg/ml for up to 1 hr at 20° C. The fibrinogen bound to the fibrinogen-binding peptide on the microspheres can be separated from the free fibrinogen by centrifugation and the amount of free and bound fibrinogen measured. The dissociation constant can then be calculated by Scatchard analysis by plotting concentration of bound fibrinogen against the ratio of the concentrations of bound: free fibrinogen, where the slope of the curve represents $K_D$.

According to some embodiments, the fibrinogen-binding peptides of the haemostatic agent, in particular peptide dendrimers, for use in compositions of the invention bind preferentially to hole 'a' of fibrinogen over hole 'b' of fibrinogen. Examples of sequences of suitable fibrinogen-binding peptides that bind preferentially to hole 'a' over hole 'b' of fibrinogen include: GPR-; GPRP- (SEQ ID NO: 1); GPRV- (SEQ ID NO: 2); GPRPFPA- (SEQ ID NO: 3); GPRVVAA- (SEQ ID NO: 4); GPRPWER- (SEQ ID NO: 5); GPRPAA- (SEQ ID NO: 6); GPRPPEC- (SEQ ID NO: 7); GPRPPER- (SEQ ID NO: 8); GPSPAA- (SEQ ID NO: 9).

According to other embodiments, the fibrinogen-binding peptides of the haemostatic agent, in particular peptide dendrimers, for use in compositions of the invention bind preferentially to hole 'b' of fibrinogen over hole 'a' of fibrinogen. Examples of sequences of fibrinogen-binding peptides that bind preferentially to hole 'b' over hole 'a' of fibrinogen include: GHR-, GHRP- (SEQ ID NO: 10), GHRPY- (SEQ ID NO: 11), GHRPL- (SEQ ID NO: 12), GHRPYamide- (SEQ ID NO: 13).

Each fibrinogen-binding peptide may, independently, be attached at its carboxy-terminal end (optionally via a linker), or at its amino-terminal end (optionally via a linker) to the carrier, or to the branched core of the dendrimer. If the fibrinogen-binding peptide is attached at its amino-terminal end, the carboxy-terminal end of the peptide may comprise an amide group. The presence of an amide group, rather than a carboxyl group (or a negatively charged carboxylate ion), at the exposed carboxy-terminal end of the peptide may help to optimise binding of the fibrinogen-binding peptide to fibrinogen.

In some embodiments, each fibrinogen-binding peptide is attached (optionally via a linker) at its carboxy-terminal end to the carrier, or to the branched core of the dendrimer. In other embodiments, at least one fibrinogen-binding peptide is attached (optionally via a linker) at its amino-terminal end to the carrier, or to the branched core of the dendrimer. For example, at least one fibrinogen-binding peptide that binds preferentially to hole 'a' over hole 'b' of fibrinogen, such as a peptide comprising sequence APFPRPG (SEQ ID NO: 14), may be attached (optionally via a linker) at its amino-terminal end to the carrier, or to the branched core of the dendrimer.

Advantageously, a haemostatic agent, or peptide dendrimer comprises fibrinogen-binding peptides of different sequence (referred to herein as a 'chimeric' haemostatic agent, or peptide dendrimer). For example, in some embodiments a haemostatic agent, or peptide dendrimer comprises fibrinogen-binding peptides that have different selectivity of binding to hole 'a' over hole 'b' of fibrinogen.

A haemostatic agent for use in compositions of the invention may comprise a plurality of carriers, wherein each carrier has a plurality of fibrinogen-binding peptides attached to the carrier, and wherein the fibrinogen-binding peptides attached to the carriers comprise fibrinogen-binding peptides of different sequence.

In some embodiments, the plurality of carriers comprise a first plurality of carriers, and a second plurality of carriers, wherein the fibrinogen-binding peptides attached to the first plurality of carriers are of different sequence to the fibrinogen-binding peptides attached to the second plurality of carriers.

In other embodiments, each carrier has fibrinogen-binding peptides of different sequence attached thereto.

In theory there is no upper limit to the number of fibrinogen-binding peptides per carrier molecule. The optimum number is likely to depend on many factors, such as the nature of the carrier, and the number of reactive groups on each carrier for attaching the fibrinogen-binding peptides. However, it is preferred that on average there are up to 100 fibrinogen-binding peptides per carrier molecule. Preferably, on average there are at least three, preferably at least four or five fibrinogen-binding peptides per carrier molecule. A preferred range is 10-20 fibrinogen-binding peptides per carrier molecule.

The carriers may comprise reactive groups which permit attachment of the fibrinogen-binding peptides. For example, the carriers may comprise thiol moieties or amine moieties on their surface. If the carriers are proteinaceous, the thiol or amine moieties may be provided by side chains of amino acids, for example cysteine or lysine. Alternatively, reactive groups may be added to the carrier. This is particularly advantageous if the carrier is formed from protein, such as albumin. For example, the carrier may be thiolated using a reagent such as 2-iminothiolane (2-IT) which is able to react with primary amine groups on the carrier. Alternatively cystamine may be coupled to carboxyl groups on the carrier in the presence of 1-Ethyl-3-(3-dimethylaminopropyl) carbodiimide hydrochloride (EDC) and N-hydroxysuccinimide (NHS), followed by reductive cleavage of the introduced disulphide bond.

In some embodiments, the fibrinogen-binding peptides are covalently immobilised to the carrier via a spacer. A preferred spacer is a non-peptide spacer, for example comprising a hydrophilic polymer such as polyethylene glycol (PEG). In a preferred embodiment, a plurality of peptide conjugates, each comprising a fibrinogen-binding peptide linked to a thiol-reactive group (for example, a maleimide group) by a PEG spacer is reacted with a thiolated carrier (for example prepared using 2-IT or cystamine as described above). Suitable non-peptide spacers are described in WO 2013/114132.

The fibrinogen-binding peptides of different sequence may comprise a first fibrinogen-binding peptide that binds preferentially to hole 'a' over hole 'b' of fibrinogen, and a second fibrinogen-binding peptide that binds with higher selectivity to hole 'a' over hole 'b' of fibrinogen than the first fibrinogen-binding peptide. Peptide dendrimers with such fibrinogen-binding peptide sequences have been found to polymerise fibrinogen rapidly over a relatively wide range of peptide dendrimer concentration.

For example, the first fibrinogen-binding peptide may comprise an amino acid sequence GPRP- (SEQ ID NO: 1) at its amino-terminal end, and/or the second fibrinogen-binding peptide may comprise an amino acid sequence -APFPRPG (SEQ ID NO: 14) at its carboxy-terminal end, where the amino acid residues of the sequences are denoted in amino- to carboxy-order, and "—" denotes the end of the sequence that is attached to the branched core of the peptide dendrimer, or to the carrier. A fibrinogen-binding peptide with the sequence -APFPRPG (SEQ ID NO: 14) at its carboxy-terminal end binds with higher selectivity to hole 'a' over hole 'b' of fibrinogen than a fibrinogen-binding peptide with the sequence GPRP- (SEQ ID NO: 1) at its amino-terminal end.

In other embodiments, the fibrinogen-binding peptides of different sequence may comprise a first fibrinogen-binding peptide that binds preferentially to hole 'a' over hole 'b' of fibrinogen, and a second fibrinogen-binding peptide that binds preferentially to hole 'b' over hole 'a' of fibrinogen. Peptide dendrimers with such fibrinogen-binding peptide sequences have been found to polymerise with fibrinogen to form relatively dense hydrogels compared to equivalent peptide dendrimers containing only fibrinogen-binding peptides that bind preferentially to hole 'a' over hole 'b' of fibrinogen. It is believed that the increased density of the hydrogels formed is due to binding of fibrinogen-binding peptides of the dendrimers to hole 'a' and hole 'b' of fibrinogen, thereby strengthening the network of polymerised fibrinogen.

For example, the first fibrinogen-binding peptide may comprise an amino acid sequence GPRP- (SEQ ID NO: 1) at its amino-terminal end and/or the second fibrinogen-binding peptide may comprise an amino acid sequence GHRP- (SEQ ID NO: 10), or an amino acid sequence GHRPY- (SEQ ID NO: 11), at its amino terminal end. Fibrinogen-binding peptides with the sequence GPRP- (SEQ ID NO: 1) at the amino-terminal end bind with some selectivity to hole 'a' of fibrinogen. Fibrinogen-binding peptides with the sequence GHRP- (SEQ ID NO: 10), or GHRPY- (SEQ ID NO: 11), at the amino-terminal end bind preferentially to hole 'b' of fibrinogen.

One or more, or each, fibrinogen-binding peptide may be covalently attached to the carrier of a haemostatic agent, for example to the branched core of a peptide dendrimer, by a non-peptide linker. The linker may be any suitable linker that does not interfere with binding of fibrinogen to the fibrinogen-binding peptides. The linker may comprise a flexible, straight-chain linker, suitably a straight-chain alkyl group. Such linkers allow the fibrinogen-binding peptides to extend away from each other. For example, the linker may comprise a —NH(CH$_2$)$_n$CO— group, where n is any number, suitably 1-10, for example 5. A linker comprising a —NH(CH$_2$)$_5$CO— group may be formed by use of ε-amino acid 6-aminohexanoic acid (εAhx).

In theory, there is no limit to the total number of fibrinogen-binding peptides that may be present in a peptide dendrimer. However, in practice, for any particular structure, the number of fibrinogen-binding peptides can be varied and tested to determine the optimum number for the desired fibrinogen polymerisation properties, for example, for the speed fibrinogen polymerisation or for the density of the hydrogel produced by polymerisation with fibrinogen. Peptide dendrimers may comprise a total of up to twenty fibrinogen-binding peptides per dendrimer, for example up to ten fibrinogen-binding peptides per dendrimer, or up to five fibrinogen-binding peptides per dendrimer.

The Applicant has found that, surprisingly, mixtures of a peptide dendrimer with a peptide conjugate, comprising two or more fibrinogen-binding peptides, are able to polymerise fibrinogen more rapidly than either the peptide dendrimer, or the peptide conjugate, alone.

Accordingly, a haemostatic agent for use in compositions of the invention may comprise a peptide dendrimer, and a peptide conjugate comprising two or more fibrinogen-binding peptides.

The peptide conjugate may comprise fibrinogen-binding peptides of the same sequence, or of different sequence. For example, the peptide conjugate may comprise only fibrinogen-binding peptides that bind preferentially to hole 'a' over hole 'b' of fibrinogen, or only fibrinogen-binding peptides that bind preferentially to hole 'b' over hole 'a' of fibrinogen, or one or more fibrinogen-binding peptides that bind preferentially to hole 'a' over hole 'b' of fibrinogen and one or more fibrinogen-binding peptides that bind preferentially to hole 'b' over hole 'a' of fibrinogen.

The peptide conjugate may comprise a carrier to which the fibrinogen-binding peptides are attached. A suitable carrier may comprise one or more amino acid residues, for example a single amino acid residue, such as a lysine amino acid residue. An advantage of conjugates comprising carriers that comprise one or more amino acid residues is that they can readily be made using solid-phase peptide synthesis methods. In addition, they may be readily produced without use of immunogenic agents and may be resistant to sterilisation.

Each fibrinogen-binding peptide of the peptide conjugate may, independently, be attached at its carboxy-terminal end (optionally via a linker), or at its amino-terminal end (optionally via a linker), to the carrier. If the fibrinogen-binding peptide is attached at its amino-terminal end, the carboxy-terminal end of the peptide may comprise an amide group.

In one example, the peptide conjugate may have the following general formula:

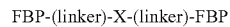

FBP-(linker)-X-(linker)-FBP where:
FBP is a fibrinogen-binding peptide;
-(linker)- is an optional linker, preferably a non-peptide linker;
X is an amino acid, preferably a multifunctional amino acid, most preferably a tri-functional amino acid residue, such as lysine, ornithine, or arginine.

The peptide conjugate may be a dendrimer. The dendrimer may comprise a branched core and a plurality of fibrinogen-binding peptides separately covalently attached to the branched core. The branched core may comprise one or more multifunctional amino acids. Each multifunctional amino acid, or a plurality of multifunctional amino acids, may have one or more fibrinogen binding peptides covalently attached to it. In some embodiments, the peptide conjugate may be a peptide dendrimer as defined above.

The fibrinogen-binding peptides of a peptide dendrimer for use in a composition of the invention may bind preferentially to hole 'a' of fibrinogen over hole 'b' of fibrinogen, and the fibrinogen-binding peptides of the peptide conjugate may bind preferentially to hole 'b' of fibrinogen over hole 'a' of fibrinogen. Such compositions have been found to have synergistic effects in that they are able to polymerise fibrinogen more rapidly than either the peptide dendrimer or the peptide conjugate alone. The mechanism of this synergistic effect is not fully understood, but without being bound by theory, it is believed that it may occur because the composition provides more 'A' and 'B' fibrinogen polymerisation sites.

Alternatively, the fibrinogen-binding peptides of a peptide dendrimer for use in a composition of the invention may bind preferentially to hole 'b' of fibrinogen over hole 'a' of fibrinogen, and the fibrinogen-binding peptides of the peptide conjugate bind preferentially to hole 'a' of fibrinogen over hole 'b' of fibrinogen.

It will be appreciated that a particular advantage of haemostatic agents for use in compositions of the invention is that they can be synthesised without use of animal-derived products, thereby minimising the risk of viral or prion infection from such products.

The biocompatible liquid used for compositions of the invention may be an aqueous or non-aqueous liquid, but is generally an aqueous liquid. Aqueous liquids may include biocompatible aqueous solutions, such as an aqueous solution of calcium chloride or sodium chloride. Generally, the biocompatible liquid will be close to physiological pH, for example in the range pH 6.0-7.5, for example, pH 7.3-7.5, or pH 7.35-7.45.

The biocompatible liquid may comprise a buffer, for example a phosphate, HEPES, or Tris buffer, such as 10-150 mM phosphate buffer, 10-150 mM HEPES buffer, or 10-150 mM Tris buffer.

The amount and average diameter of particles contained in a composition of the invention, and the relative amounts of the haemostatic agent, biocompatible liquid, and insoluble particles, is effective to provide the composition with haemostatic and physical properties, as described below.

According to certain embodiments, the particles of the composition have dimensions and other physical properties which enhance the flowability of the composition (for example, the ability to be extruded through a syringe) and the ability of the composition to flow onto and conform to sites on or in tissue, including tissue surfaces and defined cavities, such as intravertebral spaces, tissue divots, holes, or pockets.

Compositions of the invention may be partially hydrated or fully hydrated and may display a degree of swelling, for example from 0% to 100%, depending on the extent of hydration.

Exemplary and preferred size ranges for partially or fully hydrated particles are as follows:

Particle Size

|  | Exemplary Range | Preferred Range |
| --- | --- | --- |
| Partially or fully hydrated particle | 50-3000 µm | 100-1500 µm |

Compositions of the invention will usually be in partially or fully hydrated form. A dry powder (having a moisture content below 20% by weight) comprising particles of the polysaccharide may be useful as a starting material for preparation of a composition of the invention. Partially hydrated compositions of the invention, typically having from 50% to 80% hydration, are useful for applications where it is desired that the composition further swells upon application to a moist target site, for example, a tissue divot. Fully hydrated compositions are useful for applications where in situ swelling is not desired, such as in the spinal column and other areas where nerves and other sensitive structures are present.

"Target site" is the location to which a composition of the invention is to be delivered. The target site may be a site that is, or was previously, bleeding as a result of an injury or a surgical procedure. Usually, the target site will be the tissue location of interest, but in some cases the composition may be administered to a location near the location of interest, for example when the material swells in situ to cover the location of interest.

The dimensions of the particles may be achieved in a variety of ways. For example, a starting material comprising the polysaccharide may be disrupted (1) before or after cross-linking of the polysaccharide starting material or (2) before or after hydration of a cross-linked or non-cross-linked polysaccharide starting material, for example as a fully or partially hydrated material or as a dry particulate powder. The term "dry" is used herein to mean that the moisture content is sufficiently low, typically below 20% by weight water, so that the powder will be free-flowing and the individual particles will not aggregate. The term "hydrated" is used herein to mean that the moisture content is sufficiently high, typically above 50% of the equilibrium hydration level, usually in the range from 80% to 95% of the equilibrium hydration level.

Mechanical disruption of the starting material in the dry state may be preferred in cases where it is desired to control the particle size and/or particle size distribution. It may be easier to control comminution of the dry particles than the hydrated composition, and the size of the resulting reduced particles is thus easier to adjust. Conversely, mechanical disruption of a hydrated material is generally simpler and involves fewer steps than does comminution of a dry polymer starting material. Thus, disruption of a hydrated material may be preferred when the ultimate particle size and/or size distribution is not critical.

A composition of the present invention may be mechanically disrupted at the time it is delivered to a target site by extrusion through an orifice or other flow restriction, or it may be mechanically disrupted prior to delivery to a target site. Alternatively, a composition of the invention may be mechanically disrupted prior to final use or delivery. Molecular cross-linking of the polysaccharide chains can be performed before or after the mechanical disruption. The primary purpose of the mechanical disruption step is to create multiple particles having a size that enables the composition to conform to and fill the space to which it is to be delivered. Another purpose of the mechanical disruption is to facilitate passage of the composition down small diameter tubes, cannulas, and/or other applicators to the target site. When the composition is disrupted prior to use, it can be applied or administered by techniques other than extrusion, for example using a spatula or a spoon.

In some embodiments, the polysaccharide may be initially prepared (e.g. by spray drying) and/or be mechanically disrupted prior to being cross-linked, often usually prior to hydration. The polysaccharide may be provided as a finely divided or powdered dry solid which may be disrupted by further comminution to provide particles having a desired size, usually being narrowly confined within a small range. Further size selection and modification steps, such as sieving, or cyclone classification, may also be performed. For exemplary materials, the dry particle size may be in the range from 10-1500 µm, or from 50-1000 µm. An exemplary particle size distribution is such that greater than 95% by weight of the particles are in the range from 50-700 µm.

Methods for comminuting the polymeric starting material include homogenization, grinding, coacervation, milling, jet milling. Powdered polysaccharide starting materials may also be formed by spray drying. The particle size distribution may be further controlled and refined by conventional techniques such as sieving, aggregation, or further grinding. The dry powdered solid may then be suspended in an aqueous buffer, and cross-linked. In other cases, the polysaccharide may be suspended in an aqueous buffer, cross-linked, and then dried. The cross-linked, dried polysaccharide may then be disrupted, and the disrupted material subsequently resuspended in an aqueous buffer.

In an exemplary production process, a dry, non-cross-linked polysaccharide starting material is mechanically disrupted by a conventional unit operation, such as homogenization, grinding, coacervation, or milling. The powder is disrupted sufficiently to achieve dry particle sizes which produce particle sizes in the desired ranges when the product is partially or fully hydrated. The relationship between the dry particle size and the fully hydrated subunit size will depend on the swellability of the material, as discussed further below.

Alternatively, a particulate polysaccharide starting material may be formed by spray drying. Spray drying processes rely on flowing a solution through a small orifice, such as a nozzle, to form droplets which are released into a countercurrent or co-current gas stream, typically a heated gas stream. The gas evaporates solvent from the liquid starting material, which may be a solution, or dispersion. Use of spray drying to form a dry powder starting material is an alternative to mechanical disruption of the starting material. The spray drying operation will usually produce a non-cross-linked dry powder product with a highly uniform particle size. The particles may then be cross-linked, as described below.

In many instances, the mechanical disruption can be controlled sufficiently to obtain both the particle size and particle size distribution within a desired range. In other cases, however, where more precise particle size distributions are required, the disrupted material can be further treated or selected to provide the desired particle size distribution, for example by sieving, or aggregation. The mechanically disrupted polymeric starting material may then be cross-linked, as described in more detail below.

Where the particle size of a composition of the invention is less important, a dried polysaccharide starting material may be hydrated, dissolved, or suspended in a suitable buffer and cross-linked prior to mechanical disruption. Mechanical disruption will typically be achieved by passing the material through an orifice, where the size of the orifice and force of extrusion together determine the particle size and particle size distribution. While this method is often operationally simpler than the mechanical disruption of dry polysaccharide particles prior to hydration and cross-linking, the ability to control the particle size may be less precise.

In some embodiments, a composition of the invention may be packed in a syringe or other applicator prior to mechanical disruption of the particles in the composition. The materials will then be mechanically disrupted as they are applied through the syringe to the tissue target site. Alternatively, a non-disrupted, cross-linked polysaccharide starting material may be stored in a dry form prior to use. The dry material may then be loaded into a syringe or other suitable applicator, hydrated within the applicator to form a composition of the invention, and mechanically disrupted as the material is delivered to the target site, again typically being through an orifice or small tubular lumen.

A variety of biocompatible natural, semi-synthetic or synthetic polysaccharides may be used to prepare the particles used in compositions of the present invention. The particles of crosslinked polysaccharide should be substantially insoluble in the biocompatible liquid chosen for the particular composition. Suitably, the particles have a solubility of less than 10 mg particle per ml of biocompatible liquid, for example less than 1 mg/ml, or less than 0.1 mg/ml. According to some embodiments, water-insoluble particles that provide mechanical, chemical and/or biological haemostatic activity are used.

Exemplary polysaccharides include glycosaminoglycans, starch derivatives (for example oxidized starch), cellulose derivatives (for example oxidized cellulose), hemicellulose derivatives, xylan, agarose, alginate, alginate derivatives (for example oxidized alginate) chitosan, chitin, and combinations thereof.

Cross-linking of the polysaccharide may be achieved in any conventional manner. For example, polysaccharides may be cross-linked using suitable cross-linking agents.

Polysaccharide molecules may be cross-linked using bi- or poly-functional cross-linking agents which covalently attach to two or more polysaccharides. Exemplary bifunctional cross-linking agents include aldehydes, epoxies, succinimides, carbodiimides, maleimides, azides, carbonates, isocyanates, divinyl sulfone (DVS), 1,4-butanediol diglycidyl ether (BDDE), alcohols, amines, imidates, anhydrides, diazoacetate, or aziridines. Alternatively, cross-linking may be achieved by using oxidizing or other agents, such as periodates, which activate side-chains or moieties on the polysaccharide so that they may react with other side-chains or moieties to form the cross-linking bonds.

Typically, the polysaccharide molecules of the starting material will each have a molecular weight in the range from 10 kDa to 10,000 kDa, or 25 kDa to 5,000 kDa. Typically, a cross-linked polysaccharide molecule will have at least one link to another polysaccharide molecule, often having from 1 to 5 links, where the actual level of cross-linking may be selected to provide a desired rate of biodegradability.

The extent of cross-linking of the polysaccharide has an effect on several functional properties of the composition, including extrudability, absorptiveness of surrounding biological fluids, cohesiveness, ability to fill space, swelling ability, and ability to adhere to the tissue site. The extent of cross-linking should be sufficient for the insoluble particles of the polysaccharide to be able to withstand the conditions of sterilisation to be used (for example, steam or dry-heat sterilisation conditions) to sterilise a composition of the invention comprising the particles. The extent of cross-linking may be controlled by adjusting the concentration of cross-linking agent, changing the relative amounts of cross-linking agent and polysaccharide starting material, or varying reaction conditions. Typically, the degree of cross-linking is controlled by adjusting the concentration of cross-linking agent.

In some embodiments (for example, embodiments with particles comprising hyaluronic acid), the equilibrium swell of the particles may range from 0% to 500%, for example 0% to 100%.

Equilibrium swell may be controlled by varying the degree of cross-linking, which in turn is achieved by varying the cross-linking conditions, such as the type of cross-linking method, duration of exposure of a cross-linking agent, concentration of a cross-linking agent, and cross-linking temperature. Materials having differing equilibrium swell values perform differently in different applications. The ability to control cross-linking and equilibrium swell allows the compositions of the present invention to be optimized for a variety of uses.

By "percent swell," is meant the dry weight subtracted from the wet weight, divided by the dry weight and multiplied by 100, where wet weight is measured after the wetting agent has been removed as completely as possible from the exterior of the material, for example by filtration, and where dry weight is measured after exposure to an elevated temperature for a time sufficient to evaporate the wetting agent, for example 2 hours at 120° C. "Equilibrium swell," is defined as the percent swell at equilibrium after the polysaccharide material has been immersed in a wetting agent for a time period sufficient for water content to become constant, typically 18 to 24 hours.

In addition to equilibrium swell, it is also important to control the hydration of the composition immediately prior to delivery to a target site. A material with 0% hydration will be non-swollen. A material with 100% hydration will be at its equilibrium water content. Hydrations between 0% and 100% will correspond to swelling between the minimum and maximum amounts. As a practical matter, many dry, non-swollen materials will have some residual moisture content, usually below 20% by weight, more usually from 8% to 15% by weight. When the term "dry" is used herein, it specifies materials having a low moisture content where the individual particles are free flowing and generally non-swollen.

Hydration can be adjusted very simply, for example by controlling the amount of biocompatible liquid (such as an aqueous buffer) added to a dry, or partially hydrated, cross-linked material prior to use. Usually, at a minimum, it will be desirable to introduce sufficient aqueous buffer to permit extrusion through a syringe or other delivery device. In other cases, however, it may be desirable to utilize a spatula or other applicator for delivering less fluid materials. The intended use will also help determine the desired degree of hydration. In cases where it is desired to fill or seal a moist cavity, it is generally desirable to employ a partially hydrated composition which can swell and fill the cavity by absorbing moisture from the target site. Conversely, fully or substantially fully hydrated compositions are preferred for application in the brain, near the spine, and to target sites near nerves and other sensitive body structures which could be damaged by post-placement swelling. It is also be possible to prepare the compositions of the present invention with excess buffer, resulting in a two-phase composition having a fully hydrated phase and a free buffer phase.

According to some embodiments of the invention, the polysaccharide particles comprise a glycosaminoglycan (GAG). GAGs are large linear polysaccharides constructed of repeating disaccharide units with the primary configurations containing an amino sugar (either GlcNAc or GalNAc) and an uronic acid (either glucuronic acid and/or iduronic acid). A suitable glycosaminoglycan for use according to the invention is hyaluronic acid (HA), or a salt thereof.

HA is composed of alternating residues of β-D-(1→3) glucuronic acid (GlcA) and β-D-(1→4)-N-acetylglucosamine (GlcNAc). The term "hyaluronic acid" is used in literature to mean acidic polysaccharides with different molecular weights constituted by residues of D-glucuronic and N-acetyl-D-glucosamine acids, which occur naturally in cell surfaces, in the basic extracellular substances of the connective tissue of vertebrates, in the synovial fluid of the joints, in the endobulbar fluid of the eye, in human umbilical cord tissue and in cocks' combs. The term "hyaluronic acid" is used herein to include mixtures of polysaccharides with different molecular weights with alternating residues of D-glucuronic and N-acetyl-D-glucosamine acids. Hyaluronic acid is also known as hyaluronan, hyaluronate, or HA. The terms hyaluronan and hyaluronic acid are used interchangeably herein.

The content of hyaluronic acid may be determined according to the modified carbazole method (Bitter and Muir, 1962, Anal Biochem. 4: 330-334). The average molecular weight of the hyaluronic acid may be determined using standard methods in the art, such as those described by Ueno et al., 1988, Chem. Pharm. Bull. 36, 4971-4975; Wyatt, 1993, Anal. Chim. Acta 272: 1-40; and Wyatt Technologies, 1999, "Light Scattering University DAWN Course Manual" and "DAWN EOS Manual" Wyatt Technology Corporation, Santa Barbara, Calif.

The hyaluronic acid, or salt thereof, may have a molecular weight of about 10,000-10,000,000 Da, 25,000-5,000,000 Da, or 50,000-3,000,000 Da. In particular embodiments, the hyaluronic acid, or salt thereof, has a molecular weight in the range of between 300,000 and 3,000,000 Da, 400,000 and 2,500,000 Da, 500,000 and 2,000,000 Da, or 600,000 and 1,800,000 Da. In other embodiments, the hyaluronic acid, or salt thereof, has a low average molecular weight in the range of between 10,000 and 800,000 Da, 20,000 and 600,000 Da, 30,000 and 500,000 Da, 40,000 and 400,000 Da, or 50,000 and 300,000 Da.

Examples of inorganic salts of hyaluronic acid include sodium hyaluronate, potassium hyaluronate, ammonium hyaluronate, calcium hyaluronate, magnesium hyaluronate, zinc hyaluronate, and cobalt hyaluronate.

Rooster combs are a significant commercial source for hyaluronic acid. Microorganisms are an alternative source. U.S. Pat. No. 4,801,539 and EP 0,694,616 disclose fermentation methods for preparing hyaluronic acid using strains of *Streptococcus zooepidemicus*. WO 03/054163, which is incorporated herein in its entirety, describes recombinant production of hyaluronic acid or salts thereof, for example, in a Gram-positive *Bacillus* host.

U.S. Pat. No. 4,582,865 (Biomatrix Inc.) describes preparation of cross-linked gels of HA using divinyl sulfone (DVS) as the cross-linking agent. The preparation of a cross-linked HA or salt thereof using a polyfunctional epoxy compound is disclosed in EP 0 161 887 B1. Other bi- or poly-functional reagents that have been employed to cross-link HA through covalent linkages include formaldehyde (U.S. Pat. No. 4,713,448, Biomatrix Inc.), polyaziridine (WO 03/089476 A1, Genzyme Corp.), L-aminoacids or L-aminoesters (WO 2004/067575, Biosphere S.P.A.). Carbodiimides have also been reported for the cross-linking of HA (U.S. Pat. No. 5,017,229, Genzyme Corp.; U.S. Pat. No. 6,013,679, Anika Research, Inc). Total or partial cross-linked esters of HA with an aliphatic alcohol, and salts of such partial esters with inorganic or organic bases, are disclosed in U.S. Pat. No. 4,957,744.

Preferred agents for chemically cross-linking HA include divinyl sulfone (DVS), 1,2,7,8-diepoxyoctane (DEO), and 1,4-butanediol diglycidyl ether (BDDE).

Methods of making cross-linked HA gels suitable for producing particles for use in compositions of the invention are described in WO 2006/056204, US 2010/0035838, US 2010/0028437, US 2005/0136122, the contents of each of which are incorporated herein in their entirety. Production of HA-based hydrogel particles is also described in Sahiner & Jia, Turk J Chem 32 (2008), 397-409: "One-Step Synthesis of Hyaluronic Acid-Based (Sub)micron Hydrogel Particles: Process Optimization and Preliminary Characterization".

For example, WO 2006/056204 describes a method of producing a hydrogel comprising hyaluronic acid, or salt thereof, crosslinked with divinylsulfone (DVS). The method comprises the steps of: (a) providing an alkaline solution of hyaluronic acid, or salt thereof; (b) adding DVS to the solution of step (a), whereby the hyaluronic acid, or salt thereof, is crosslinked with the DVS to form a gel; and (c) treating the gel of step (b) with a buffer, wherein the gel swells and forms a hydrogel comprising hyaluronic acid, or salt thereof, crosslinked with DVS.

The hyaluronic acid, or salt thereof, may have an average molecular weight of between 100 and 3,000 kDa, for example between 500 and 2,000 kDa, or between 700 and 1,800 kDa. DVS may be added to the solution of step (a) in a weight ratio of between 1:1 and 100:1 of HA/DVS (dry weight), preferably between 2:1 and 50:1 of HA/DVS (dry weight), for example 2.5:1 to 8:1, or 5:1 HA/DVS (dry weight).

Suitable cross-linked HA hydrogel may be produced using Novozyme's Hyasis Link technology for preparing cross-linked HA gels. Novozymes also offers Hyasis, a *Bacillus*-derived hyaluronic acid, obtained from a recombinant manufacturing process based on fermentation of non-pathogenic bacterial strain *Bacillus subtilis*. The process uses no animal-derived raw materials.

A cross-linked HA hydrogel may be micronized, for example using any of the mechanical disruption methods described above, to provide particles of a suitable size for use in compositions of the invention. In a particular embodiment, a cross-linked HA hydrogel is micronized by grinding, and cross-linked HA hydrogel particles of a suitable size are selected by sieving the ground product.

Suitable cross-linked HA hydrogel particles for use according to the invention have an average diameter (when partially or fully hydrated) of approximately 100-1500 µm, or 100-1000 µm. An example is cross-linked HA hydrogel particles comprising HA 2.7% w/v; cross-linking 5:1 of HA:DVS, with average hydrogel particle size approximately 400 µm.

A particular disadvantage of conventional gelatin-based haemostats is that the gelatin matrix is opaque. This can hinder visibility making accurate administration to the wound site, and monitoring of the extent to which bleeding has been controlled, more difficult. The applicant has found that removal of air bubbles from a paste comprising cross-linked polysaccharide particles, in particular an aqueous paste comprising cross-linked HA hydrogel particles, for example by centrifuging the paste, dramatically reduces its opacity, and provides a substantially transparent paste. Bleeding of a wound or suture line can be observed through the transparent paste. This enables a surgeon to monitor haemostasis more effectively, and to intervene more rapidly if necessary.

According to a further aspect of the invention, there is provided a method of reducing opacity of a composition comprising insoluble particles of a cross-linked biocompatible polysaccharide dispersed throughout a biocompatible liquid phase, which comprises centrifuging the composition to remove air bubbles from the composition.

There is further provided a substantially transparent composition comprising insoluble particles of a cross-linked biocompatible polysaccharide dispersed throughout a biocompatible liquid phase. The liquid phase may be provided by a biocompatible liquid as described above.

Such transparent compositions may be used in haemostatic compositions of the invention, thereby providing a substantially transparent haemostatic composition of the invention. For example, a substantially transparent haemostatic composition of the invention may be formed by mixing a soluble haemostatic agent comprising a plurality of carriers and a plurality of fibrinogen-binding peptides immobilised to each carrier, with a substantially transparent composition comprising insoluble particles of a cross-linked biocompatible polysaccharide suitable for use in haemostasis dispersed throughout a biocompatible liquid phase.

Alternatively, a substantially transparent haemostatic composition of the invention may be formed by removing air bubbles from a haemostatic composition of the invention. The air bubbles may be removed from the haemostatic composition by any suitable method, for example by centrifugation.

There is further provided according to the invention a substantially transparent haemostatic composition comprising a soluble haemostatic agent comprising: a plurality of carriers and a plurality of fibrinogen-binding peptides immobilised to each carrier; a biocompatible liquid; and particles of a cross-linked biocompatible polysaccharide suitable for use in haemostasis and which are insoluble in the biocompatible liquid.

A composition of the invention is considered to be transparent if a surgical suture of 1 mm diameter or less, for example at least 0.5 mm, 0.4 mm, 0.3 mm, 0.2 mm, or 0.1 mm diameter, is visible through a 3 mm thickness of the composition.

Compositions of the invention may further comprise a pharmaceutically acceptable excipient or diluent. Suitable pharmaceutically acceptable excipients and diluents are well-known to the skilled person. Pharmaceutically acceptable excipients and diluents include those suitable for topical administration with a composition of the invention to a wound site. Suitable pharmaceutically acceptable diluents or excipients include buffers, such as Tris-HCl, acetate, or phosphate buffers, additives such as detergents or solubilizing agents (for example, Tween 80, Polysorbate 80), antioxidants (for example, ascorbic acid, sodium metabisulfite), preservatives (for example, meta-cresol, parabens (methyl, propyl, or butyl), chlorobutanol, phenylmercuric salts (for example, acetate, borate, nitrate), sorbic acid, benzyl alcohol), and bulking substances (for example, lactose, mannitol), tonicity agents (for example, sugars, sodium chloride), polymeric compounds, such as polylactic acid, polyglycolic acid.

Compositions of the invention may further include additives to facilitate the preparation of the composition, enhance physical and mechanical properties, enhance the haemostatic properties of the composition or provide antimicrobial properties. For example, compositions of the invention may further comprise effective amounts of one or more additives or compounds, such as bioactive component(s) to be delivered to the patient, viscosity modifiers, such as carbohydrates and alcohols, materials to control the rate of resorption, surfactants, antioxidants, humectants, wetting agents, lubricants, thickeners, diluents, irradiation stabilizers (for example, radical scavengers), plasticizers, or stabilizers. For example, glycerol may be added to enhance the extrudability or injectability of the composition. When utilized, glycerol may be present in the compositions from about 0% to about 20%, or from about 1% to about 10% or about 5%, by weight of glycerol, based on the weight of the liquid phase.

Exemplary bioactive components include, but are not limited to, proteins, carbohydrates, nucleic acids, and inorganic and organic biologically active molecules such as enzymes, antineoplastic agents, antimicrobial agents, such as bacteriostatic agents, bacteriocidal agents, antibiotics, antiviral agents, local anaesthetics, anti-inflammatory agents, hormones, anti-angiogenic agents, antibodies, neurotransmitters, psychoactive drugs, drugs affecting reproductive organs and oligonucleotides, such as antisense oligonucleotides. Such bioactive components will typically be present at relatively low concentrations, typically below 10% by weight of the compositions, usually below 5% by weight, and often below 1% by weight.

By "effective amount", it is meant that amount necessary to provide to the compositions those properties for which the additive is being added. The effective amount also is limited by the maximum amount that may be added without causing detrimental biological affects.

The biocompatible liquid and particles of compositions of the invention are typically present in relative amounts effective to provide a composition, for example a paste, or slurry, suitable for use in providing haemostasis. In certain embodiments, the weight ratio of particles to liquid is from about 1:1 to about 1:12, or from about 1:3 to about 1:8 or about 1:5. Compositions of the present invention will typically have a solids content in the range from 1% by weight to 70% by weight, for example from 5% by weight to 20% by weight, or from 5% by weight to 16% by weight. For compositions having a higher solid content, typically above 16% by weight, a plasticizer may be included in the composition, typically from 0.1% by weight to 30% by weight, or from 1% by weight to 5% by weight. Suitable plasticizers include polyethylene glycols, sorbitol, and glycerol.

According to the invention, there is also provided a method of polymerising fibrinogen, which comprises contacting fibrinogen with a composition of the invention.

The relative concentration of the composition and the fibrinogen used for polymerisation will depend on the nature of the composition, for example how many fibrinogen-binding peptides are present, and the sequence of the fibrinogen-binding peptides. The Applicant has observed rapid polymerisation times using peptide dendrimers at concentrations ranging from 0.005 mg/ml to 2 mg/ml with physiological levels of fibrinogen (3 mg/ml).

For some peptide dendrimers, as the concentration of the dendrimer is increased, the speed of fibrinogen polymerisation (i.e. the "clotting time") is reduced. Without being bound by theory, this is believed to be due to saturation of the 'a' and/or 'b' holes of the fibrinogen molecules by the fibrinogen-binding peptides of the dendrimer. At these higher dendrimer concentrations, there is an excess of fibrinogen-binding peptides competing for free fibrinogen binding holes (i.e. for empty 'a' and/or 'b' holes), and this competition is believed to reduce the rate at which polymerisation takes place.

There is also provided according to the invention a kit for treating bleeding, which comprises a composition of the invention, and, separately, fibrinogen.

The composition may polymerise endogenous (i.e. host) fibrinogen present at the target site. In some embodiments, exogenous fibrinogen may be administered as well as the composition of the invention to the target site.

The term "fibrinogen" is used herein to include natural fibrinogen, recombinant fibrinogen, or a derivative of fibrinogen that can be converted by thrombin to form fibrin (for example, natural or recombinant fibrin monomer, or a derivative of fibrin monomer that may or may not be capable of spontaneous assembly). The fibrinogen should be able to bind at least two fibrinogen binding peptides. The fibrinogen may be obtained from any source, and from any species (including bovine fibrinogen), but is preferably human fibrinogen. Human fibrinogen may be obtained from autologous or donor blood. Autologous fibrinogen, or recombinant fibrinogen, is preferred because this reduces the risk of infection when administered to a subject.

A suitable amount of a composition of the invention for administration to a human subject will depend, for example, on the type of haemostatic agent, for example how many fibrinogen-binding peptides are present per carrier molecule, and on the type and size of wound or bleeding site. However, a typical amount of the haemostatic agent is 0.1 ml to 50 ml, for example 0.1 ml to 5 ml, 1 to 50 ml, or 1 to 5 ml, of a composition containing the haemostatic agent at a concentration of 0.005 to 25 mg/ml, for example 0.01 to 10 mg/ml.

A suitable amount of exogenous fibrinogen for administration to a human subject is from 0.1 mg to 120 mg, for example 3 mg to 120 mg.

Compositions of the invention have several important advantages. In particular, in certain embodiments, the haemostatic agent can readily be manufactured using conventional solid-phase peptide synthesis procedures. This minimises the risk of viral or prion infection from such products. At optimum concentrations, the haemostatic agent of compositions of the invention can polymerise fibrinogen, in the absence of thrombin, in less than a second. The haemostatic agent of compositions of the invention can also polymerise fibrinogen in human plasma in less than a second.

The structure of a haemostatic agent for use in a composition of the invention can be selected so as to optimise its properties for the intended use of the composition. For example, a peptide dendrimer comprising five fibrinogen-binding peptides of the same sequence that bind preferentially to the 'a' hole of fibrinogen is able to polymerise fibrinogen almost instantaneously. In contrast, a 'chimeric' peptide dendrimer with one or more fibrinogen-binding peptides that bind preferentially to the 'a' hole of fibrinogen, and one or more different fibrinogen-binding peptides that bind preferentially to the 'b' hole of fibrinogen, may polymerise fibrinogen more slowly, but forms hydrogels of greater density and size.

It has been found that the haemostatic agents in compositions of the invention (especially compositions of the invention in which the biocompatible liquid is an aqueous liquid) are surprisingly resistant to sterilization, particularly steam sterilization, and dry-heat sterilization. Consequently, compositions of the invention may be sterilized using conventional sterilization methods without significant loss of haemostatic activity, especially without significant loss of the ability of the haemostatic agent of the composition to polymerise with fibrinogen. This is an important advantage because it allows the compositions to be provided as hydrated, sterile, ready-to-use, flowable haemostatic compositions. The compositions may be prepared well in advance of the time of use, while maintaining haemostatic activity, even after being subjected to heat or steam sterilization.

As used herein, "sterile" means substantially free of viable germs and/or microorganisms and as further recognized and described by governmental standards pertaining to compositions and medical devices described and claimed herein.

Suitable conventional methods of sterilization include using saturated steam under pressure ("steam sterilization"), or dry-heat sterilization.

Exposure of microorganisms to saturated steam under pressure in an autoclave causes irreversible denaturation of enzymes and structural proteins. An autoclave is a pressure chamber used for sterilization by subjecting the contents of the autoclave to high pressure saturated steam, for example at 121° C. (249° F.) for around 15-20 minutes. The temperature at which denaturation occurs varies inversely with the amount of water present. The air should be evacuated from the autoclave before admission of steam. This method is particularly suitable for aqueous preparations and for surgical dressings and medical devices.

According to the invention, there is provided a method of sterilising a composition of the invention, which comprises exposing the composition to saturated steam under pressure, under conditions of time, temperature, and pressure that are effective to sterilise the composition. Suitable conditions for sterilization using saturated steam under pressure in an autoclave are: at least 15 minutes at 121-124° C. (200 kPa), at least 10 minutes at 126-129° C. (250 kPa), or at least 5 minutes at 134-138° C. (300 kPa).

In dry-heat sterilization processes, the primary lethal process is believed to be oxidation of cell constituents. Dry-heat sterilization requires a higher temperature than moist heat and a longer exposure time. The method is, therefore, more convenient for heat-stable, non-aqueous materials that cannot be sterilized by steam because of its deleterious effects or failure to penetrate.

According to the invention, there is provided a method of sterilising a composition of the invention, which comprises exposing the composition to dry heat, under conditions of time and temperature that are effective to sterilise the composition. Suitable temperatures and times for dry-heat sterilization are: 160° C. for 180 minutes, 170° C. for 60 minutes, or 180° C. for 30 minutes. Other conditions may be necessary for different preparations to ensure the effective elimination of all undesirable microorganisms. The oven should normally be equipped with a forced air system to ensure even distribution of heat throughout all the materials processed.

According to the invention there is also provided a composition of the invention, which is sterile. Sterile compositions of the invention may have been sterilised by any suitable method, most suitably by steam sterilization or dry-heat sterilization.

The applicant has found that haemostatic agents for use in compositions of the invention retain ability to polymerise fibrinogen after sterilisation in an autoclave for 25 minutes at 121° C., and remain stable when stored for at least thirteen weeks at 40° C. The applicant has also found that compositions of the invention retain ability to polymerise fibrinogen after sterilisation in an autoclave for 25 minutes at 121° C., and remain stable when stored for at least two weeks at 40° C. The storage temperature of 40° C. is used for accelerated stability studies, and is predictive of storage for longer periods at temperatures typically prevailing during storage of pharmaceutical products, for example room or fridge temperature.

Compositions of the invention may advantageously be provided as sterile, ready-to-use, flowable formulations. Such compositions may be provided in a suitable applicator for administration of the composition to a target site.

Compositions of the invention may be applied using an applicator, such as a syringe, a spatula, a brush, a spray, manually by pressure, or by any other conventional technique.

Usually, the compositions will be applied using a syringe or similar applicator capable of extruding the composition through an orifice, aperture, needle, tube, or other passage to form a bead, layer, or similar portion of material. Mechanical disruption of the composition can occur as the composition is extruded through an orifice in the syringe or other applicator, typically having a size in the range from 0.01 mm to 5.0 mm, preferably 0.5 mm to 2.5 mm. Typically, however, the particles in the composition will have been prepared from a powder having a desired particle size (which upon hydration yields particles of the requisite size), or will be partially or entirely mechanically disrupted to the requisite size prior to a final extrusion or other application step.

Medical devices in which a haemostatic composition of the present invention may be utilized include any device suitable for applying a flowable or injectable haemostatic paste to a target site requiring haemostasis. Examples of devices or applicators include syringes, such as Becton Dickinson or Monoject luer syringes. Other suitable devices are disclosed in detail in U.S. Pat. No. 6,045,570, the contents of which are incorporated by reference in their entirety.

The compositions may be applied at varying degrees of hydration, usually but not necessarily being at least partially hydrated. When applied at their equilibrium hydration level, the compositions will display substantially equilibrium hydration and little or no swelling when applied to tissue. In some embodiments, the composition is delivered to the patient at a hydration level below its equilibrium swell. The particles in the composition may swell by 10 to 20% upon contact with blood or body fluids. Swelling of the partially hydrated compositions results from absorption of moisture from the tissue and surroundings to which the composition is applied.

The present invention further provides kits comprising a composition of the invention and written instructions for administering the composition to a target site. The composition and written instructions will be included together in a conventional container, such as a box, jar, pouch, or tray. The written instructions may be printed on a separate sheet of paper or other material and packaged on or within the container or may be printed on the container itself. Usually, the composition(s) will be provided in a separate, sterile syringe, or other applicator, or in a separate bottle, jar, or vial. If a composition of the invention is provided in non-hydrated form, the kit may optionally include a separate container with a suitable aqueous buffer for hydration. If a composition of the invention is not provided in an applicator, a suitable applicator, e.g. a syringe, may also be provided.

According to the invention, there is also provided a method of making a haemostatic composition of the invention, which comprises mixing together a biocompatible liquid, a soluble haemostatic agent, and particles of a cross-linked biocompatible polysaccharide suitable for use in haemostasis and which are insoluble in the biocompatible liquid, wherein the soluble haemostatic agent comprises a plurality of carriers and a plurality of fibrinogen-binding peptides immobilised to each carrier.

In particular embodiments, the biocompatible liquid, the soluble haemostatic agent, and the particles are mixed together under conditions effective to form a continuous liquid phase comprising the particles substantially homogeneously dispersed throughout the liquid phase, thereby forming a substantially homogeneous haemostatic composition.

The biocompatible liquid, soluble haemostatic agent, and particles may be mixed together in any order, or at substantially the same time. For example, in one embodiment, the biocompatible liquid and particles may be mixed together to form a substantially homogeneous paste in which the particles are dispersed throughout the liquid, and the soluble haemostatic agent may then be added and mixed with the paste to form the haemostatic composition. For example, a solution of the haemostatic agent in the biocompatible liquid, or other liquid (but preferably water or an aqueous liquid, such as an aqueous buffer) may be added to the substantially homogeneous paste and mixed with the paste to form the haemostatic composition. Optionally, the homogeneous paste may be centrifuged to remove air bubbles prior to, or after, addition of the soluble haemostatic agent. In an alternative embodiment, the soluble haemostatic agent may be dissolved in, or mixed with the biocompatible liquid, and the particles may then be added to the mixture, and mixed to form the haemostatic composition. Optionally, the haemostatic composition may then be centrifuged to remove air bubbles. In a further embodiment, the soluble haemostatic agent and the particles may be added to the biocompatible liquid at substantially the same time, or immediately one after the other, and then mixed to form the haemostatic composition. Optionally, the composition may then be centrifuged to remove air bubbles. Removal of air bubbles will reduce the opacity of the composition, rendering it substantially transparent.

The haemostatic composition may be sterilized, for example by steam sterilisation or dry-heat sterilisation.

In some embodiments of the invention, a haemostatic composition of the invention may be formulated into a hydrated, flowable paste or slurry, and packaged into an applicator (for example, a syringe or other applicator as described above), which is then sterilized to provide a sterile, ready-to-use, flowable haemostatic composition.

Thus, according to the invention there is provided an applicator comprising a sterile, ready-to-use, flowable haemostatic composition of the invention.

The applicator with the composition packaged inside may be sterilised by any suitable method, most suitably by steam sterilisation or dry-heat sterilisation.

Compositions of the invention may have sealing properties in addition to haemostatic effect. The compositions may be applied prophylactically to a wound that is not or hardly bleeding and will form a cohesive, protective barrier over the wound, thereby helping the wound to heal.

According to the invention there is provide a haemostatic composition of the invention for use as a medicament.

There is also provided according to the invention a haemostatic composition of the invention for use in the treatment of bleeding, or for use in the treatment of a wound.

There is further provided according to the invention use of a haemostatic composition of the invention in the manufacture of a medicament for the treatment of bleeding, or for the treatment of a wound.

There is also provided according to the invention a method of treating bleeding, which comprises administering an effective amount of a haemostatic composition of the invention to a bleeding wound.

There is further provided according to the invention a method of treating a wound, which comprises administering an effective amount of a haemostatic composition of the invention to a wound.

An effective amount of a composition of the invention for administration to a subject, such as a human subject, will depend, for example, on the type of haemostatic agent, for example how many fibrinogen-binding peptides are present per carrier molecule, and on the type and size of wound or bleeding site. However, a typical effective amount of the composition is 0.1 ml to 50 ml, for example 0.1 ml to 5 ml, 1 to 50 ml, or 1 to 5 ml, of a composition containing the haemostatic agent at a concentration of 0.005 to 25 mg/ml, for example 0.01 to 10 mg/ml.

Embodiments of the invention are now described by way of example only, with reference to the accompanying drawings in which.

Figure 9:
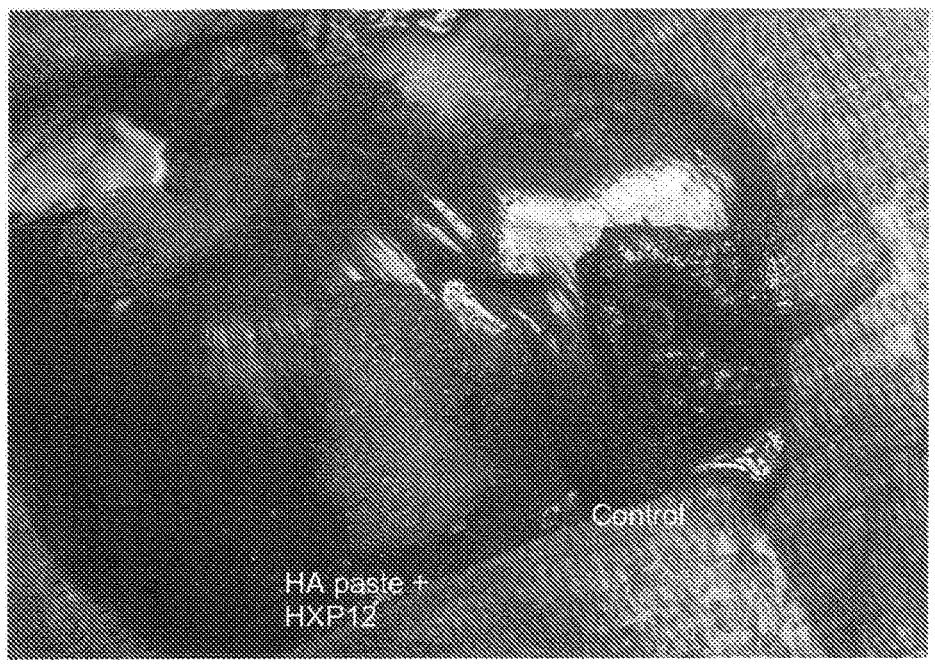
Figure 10:
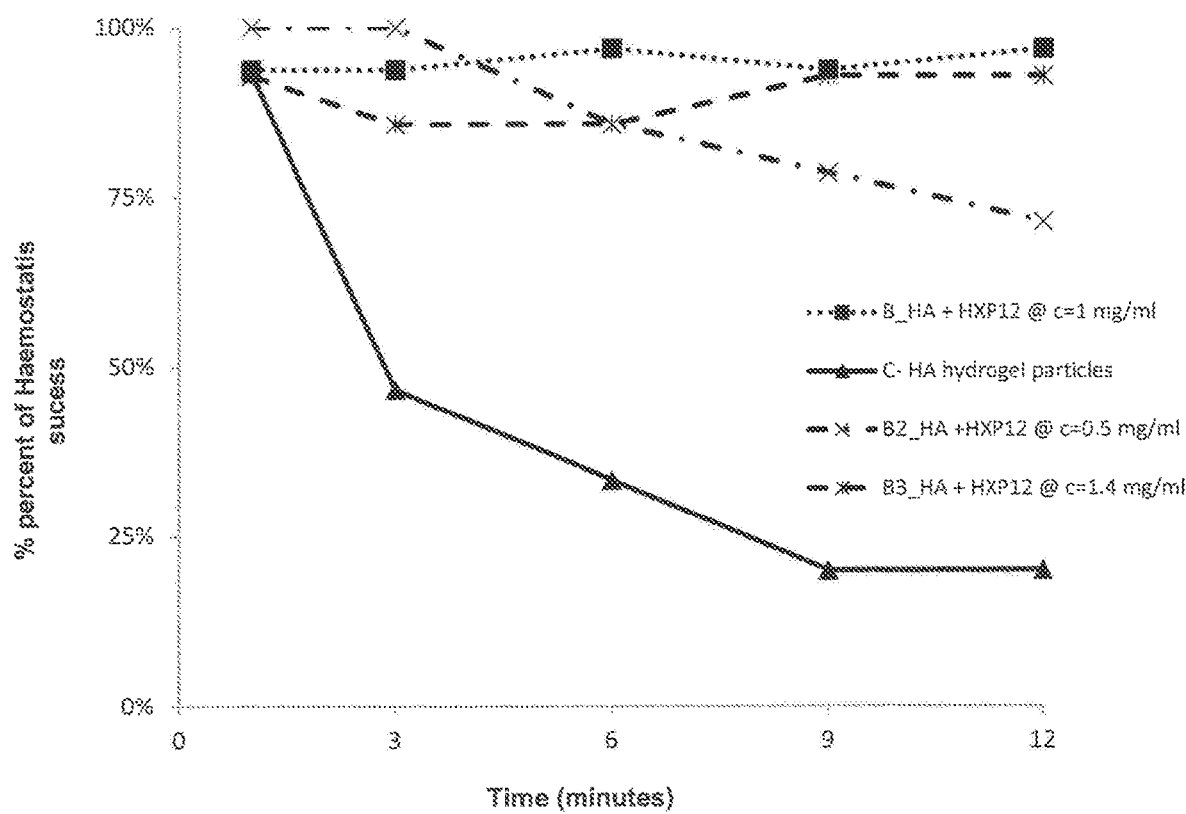
Figure 11:
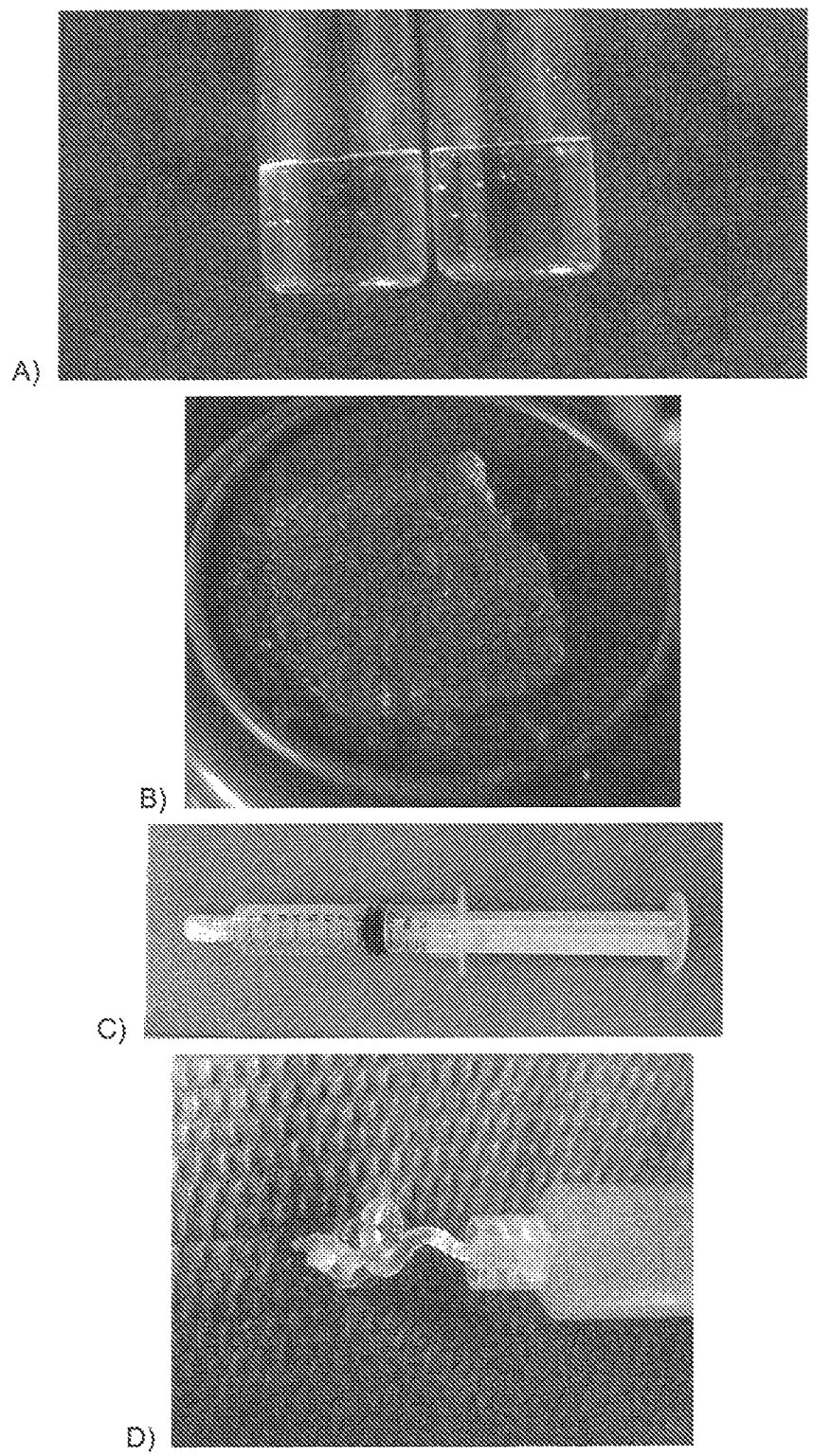
Figure 11:
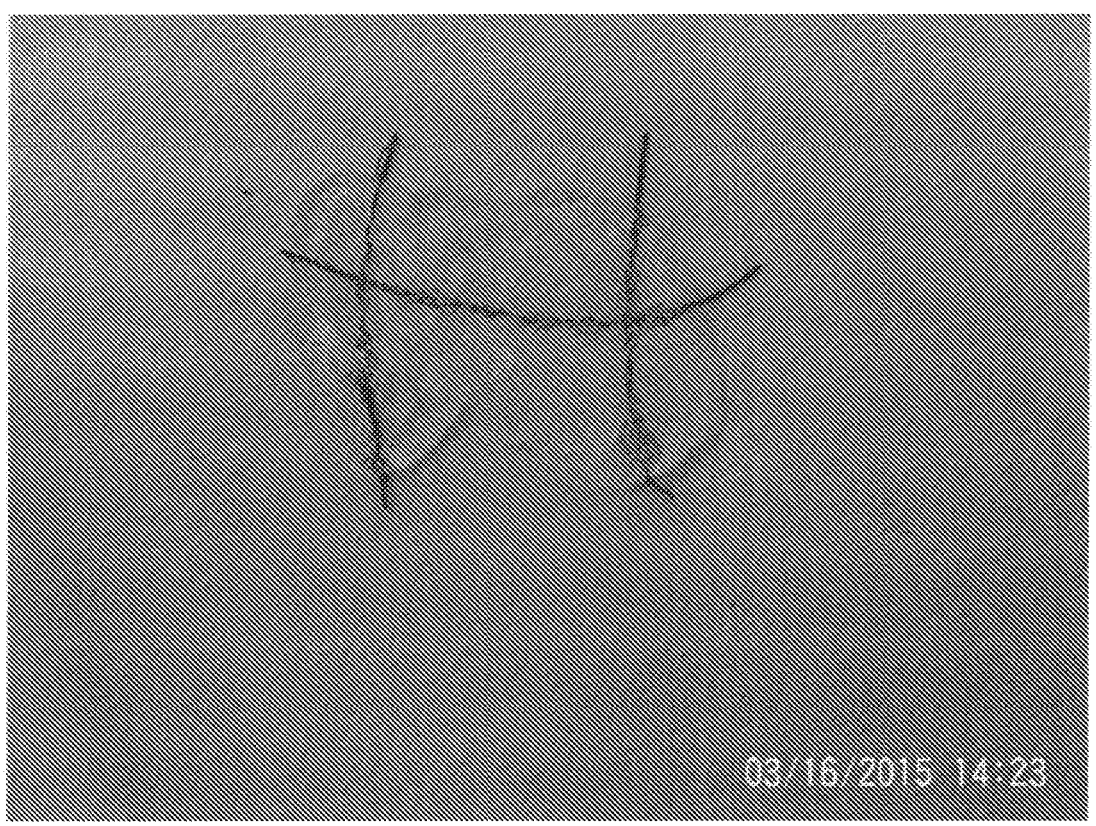

FIG. 9 is a photograph of a biopsied rabbit liver. A biopsy site treated with a control is shown above the label "Control". A biopsy site treated with a composition according to an embodiment of the invention is shown above the label "HA paste+HXP12";

FIG. 10 shows a plot of the haemostatic effect (% haemostatic success) of different embodiments of a composition of the invention in treating bleeding of biopsied rabbit liver, compared with a control, over time; and FIG. 11A shows a photograph of a transparent paste containing cross-linked hyaluronic acid gel particles. FIG. 11B shows a photograph of an embodiment of a composition of the invention formed by mixing the transparent paste with a haemostatic agent. FIG. 11C shows a photograph of a syringe containing an embodiment of a composition of the invention which has been sterilized in situ. FIG. 11D shows a photograph of an embodiment of a composition of the invention that has been extruded through a syringe. FIG. 11E shows a photograph of an embodiment of a transparent composition of the invention that has been deposited over surgical suture material.

EXAMPLE 1

Synthesis of Peptide Dendrimers and Peptide Conjugates

Peptides were synthesised on Rink amide MBHA low loaded resin (Novabiochem, 0.36 mmol/g), by standard Fmoc peptide synthesis, using Fmoc or Boc protected amino acids (Novabiochem).

In general, single-coupling cycles were used throughout the synthesis and HBTU activation chemistry was employed (HBTU and PyBOP (from AGTC Bioproducts) were used as the coupling agents). However, at some positions coupling was less efficient than expected and double couplings were required.

The peptides were assembled using an automated peptide synthesiser and HBTU up to the branch points and by manual peptide synthesis using PyBOP for the peptide branches.

For automated synthesis a threefold excess of amino acid and HBTU was used for each coupling and a ninefold excess of diisopropylethylamine (DIPEA, Sigma) in dimethylformamide (DMF, Sigma).

For manual synthesis a threefold excess of amino acid and PyBOP was used for each coupling and a ninefold excess of DIPEA in N-methylpyrollidinone (NMP, Sigma).

Deprotection (Fmoc group removal) of the growing peptide chain using 20% piperidine (Sigma) in DMF likewise may not always be efficient and require double deprotection.

Branches were made using Fmoc-Lys(Fmoc)-OH, Fmoc-Lys(Boc)-OH, or Fmoc-Lys(Mtt)-OH.

Final deprotection and cleavage of the peptide from the solid support was performed by treatment of the resin with 95% TFA (Sigma) containing triisopropylsilane (TIS, Sigma), water and anisole (Sigma) (1:1:1, 5%) for 2-3 hours.

The cleaved peptide was precipitated in cold diethyl ether (Sigma) pelleted by centrifugation and lyophilized. The pellet was re-dissolved in water (10-15 mL), filtered and purified via reverse phase HPLC using a C-18 column (Phenomenex at flow rate 20 ml/min) and an acetonitrile/water gradient containing 0.1% TFA. The purified product was lyophilized and analyzed by ESI-LC/MS and analytical HPLC and were demonstrated to be pure (>95%). Mass results all agreed with calculated values.

Peptide Dendrimers and Peptide Conjugates

The structures of peptide dendrimers and peptide conjugates synthesised using the methods described above are shown below.

The "$NH_2$—" group at the end of a peptide sequence denotes an amino group at the amino-terminal end of the sequence. The "-am" group at the end of a peptide sequence denotes an amide group at the carboxy-terminal end of the sequence.

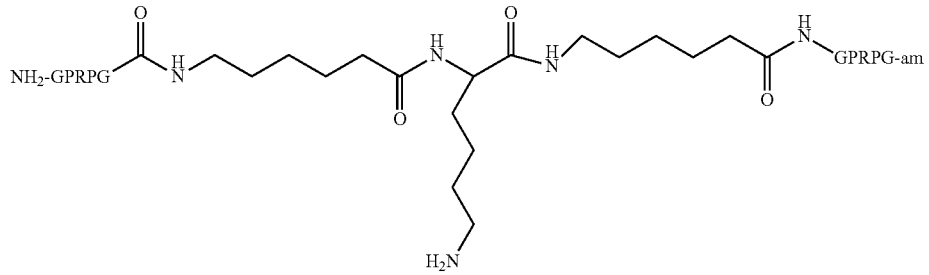

Peptide Conjugate No. 1

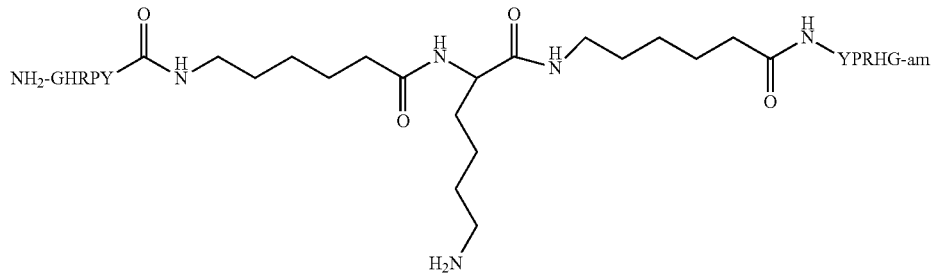

Peptide Conjugate No. 2

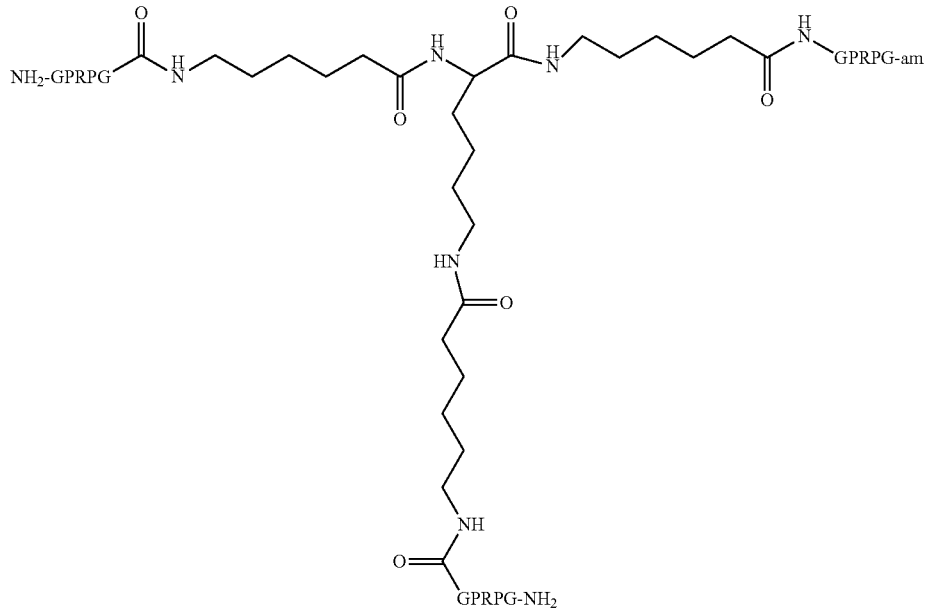

Peptide Dendrimer No. 3

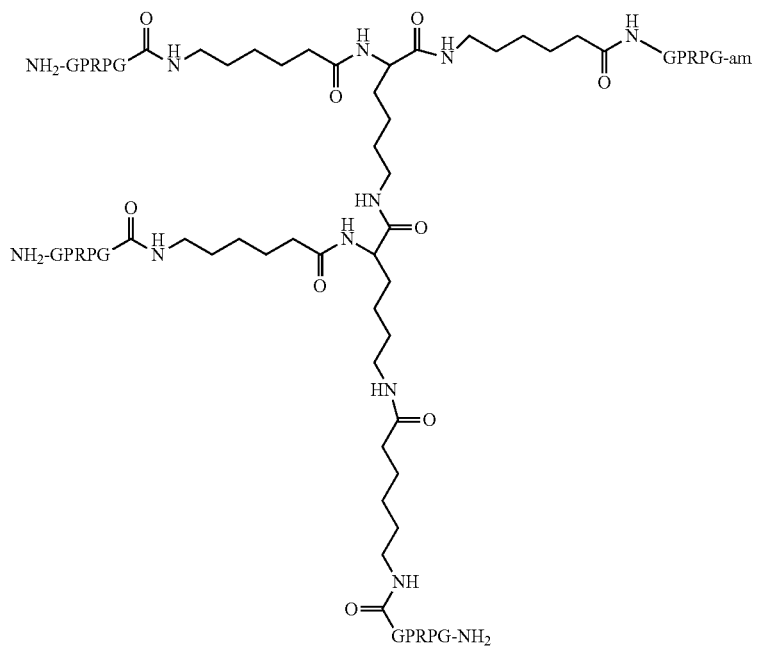
Peptide Dendrimer No. 4
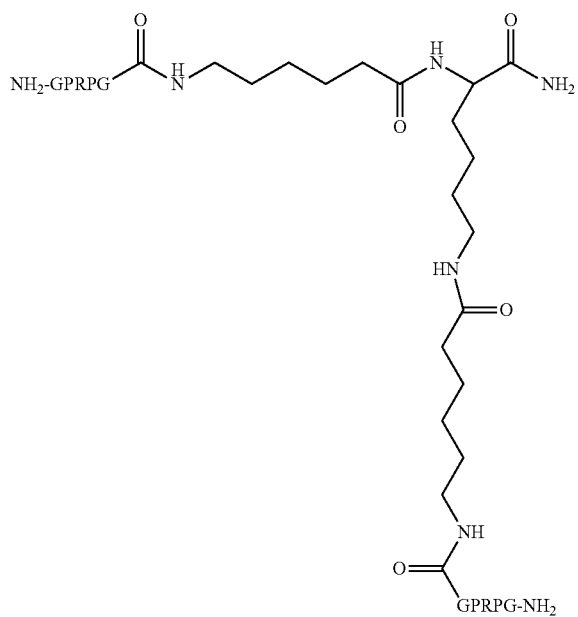
Peptide Dendrimer No. 5

Peptide Dendrimer No. 8
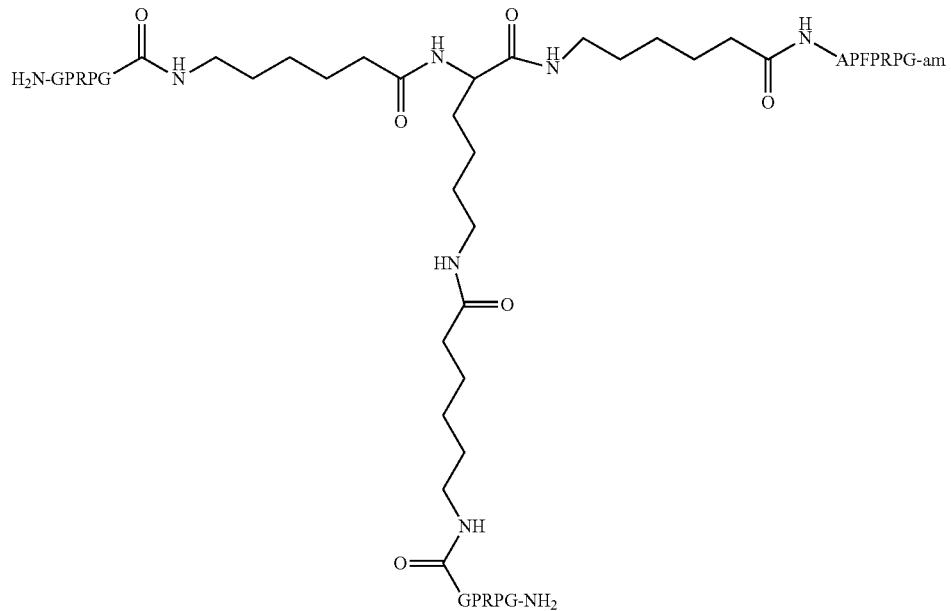
Peptide Dendrimer No. 9
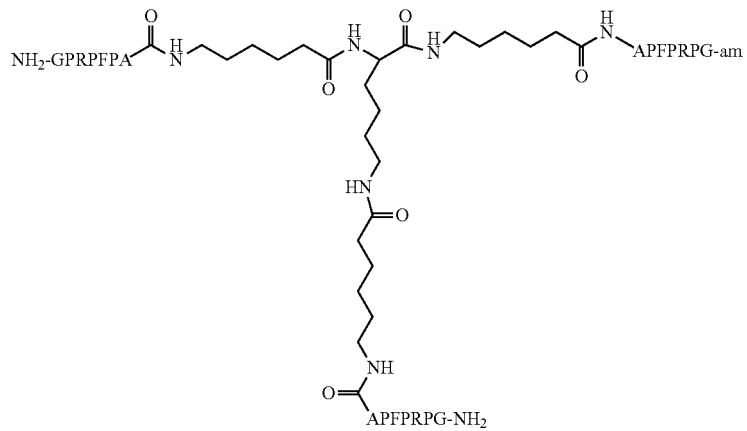
Peptide Dendrimer No. 10
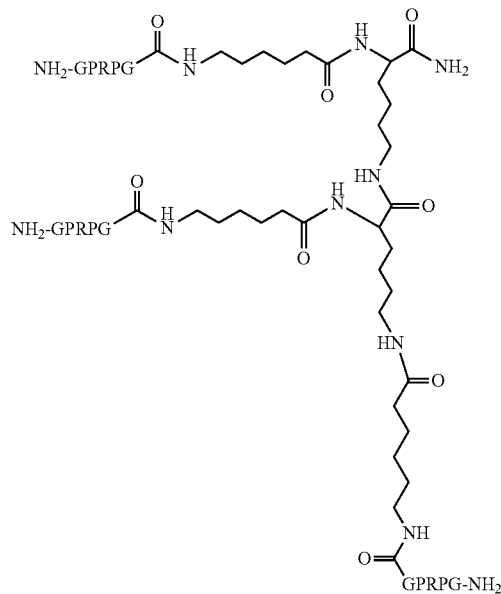

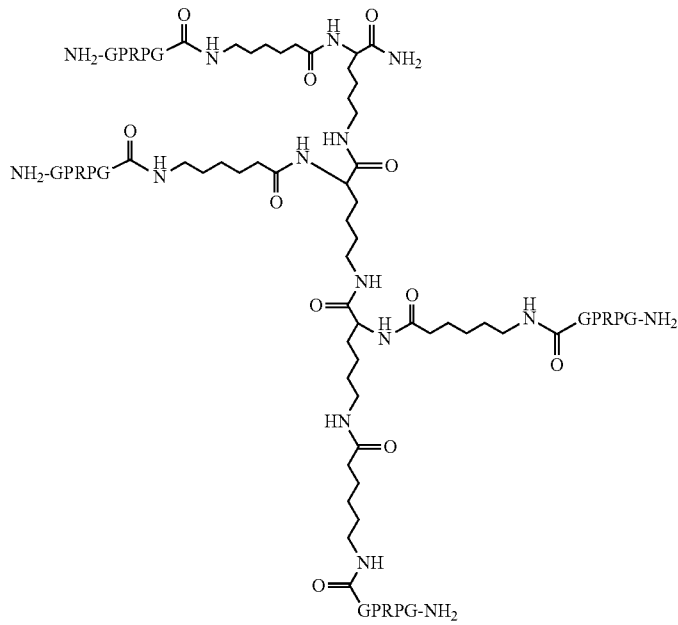
Peptide Dendrimer No. 11
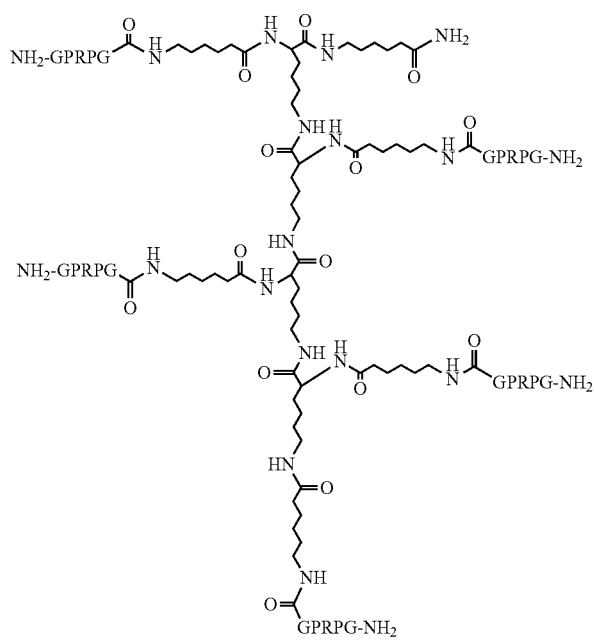
Peptide Dendrimer No. 12

-continued

Peptide Dendrimer No. 13

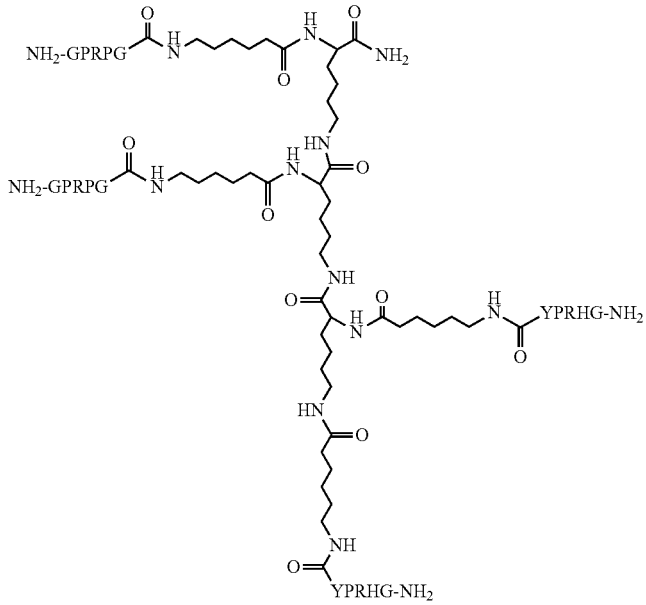

EXAMPLE 2

Copolymerisation of a Peptide Dendrimer with Fibrinogen

Dendrimer No. 12 comprises a branched core with four consecutive lysine residues. The lysine residues are covalently linked through a side chain of an adjacent lysine residue.

Figure 1:
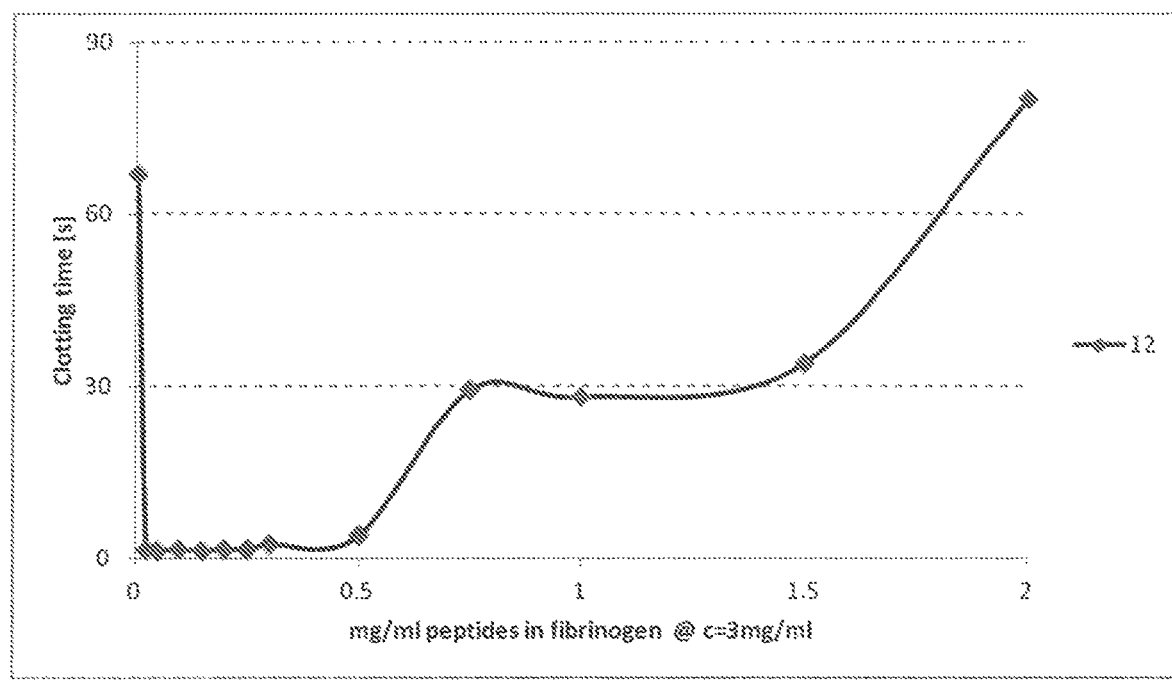
FIG. 1 shows the ability of a peptide dendrimer for use in a preferred embodiment to polymerise fibrinogen at varying concentrations.

The ability of Peptide Dendrimer No. 12 to polymerise fibrinogen was assessed. 30 μl of dendrimer in solution, at concentration ranging from 0.005-2 mg/ml, was added to 100 μl purified human fibrinogen at 3 mg/ml (the level of fibrinogen found in the blood). Polymerisation of fibrinogen was analysed using a Sigma Amelung KC4 Delta coagulation analyser. FIG. 1 shows a plot of the polymerisation (clotting) times (in seconds) with increasing concentration of dendrimer.

The results show that the dendrimer was able to copolymerise with fibrinogen almost instantaneously, even at very low concentrations of dendrimer. The increase in clotting time with dendrimer concentrations above 0.5 mg/ml is thought to be explained by an excess of fibrinogen-binding peptides compared to the number of free binding pockets in fibrinogen. At higher concentrations, the fibrinogen-binding peptides of the dendrimer may saturate the fibrinogen binding pockets, resulting in a significant number of excess dendrimer molecules that are not able to copolymerise with fibrinogen.

EXAMPLE 3

Effect of Varying the Number of Fibrinogen-Binding Peptides Per Dendrimer on the Speed of Copolymerisation with Fibrinogen This example investigates the effect of varying the number of fibrinogen-binding peptides per peptide dendrimer on the speed of copolymerisation with fibrinogen.

Figure 2:
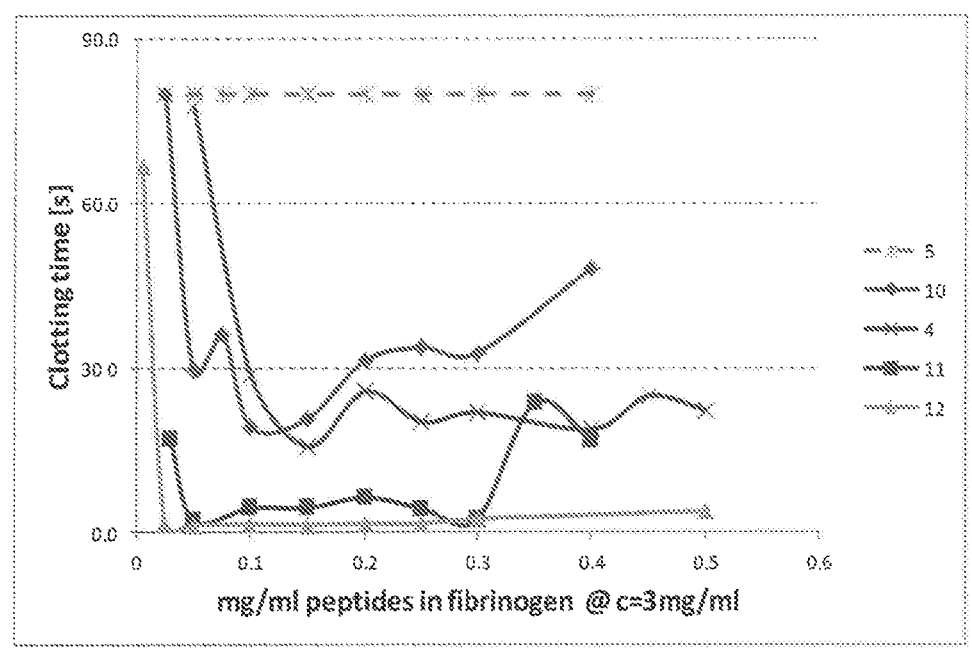
FIG. 2 shows the ability of several different peptide dendrimers to polymerise fibrinogen at varying concentrations. The numbering refers to the identity of the peptide dendrimer.

The ability of Peptide Dendrimer Nos. 4, 5, 10, 11, and 12 to copolymerise with fibrinogen was assessed using the same method described in Example 2. The concentration of each dendrimer was varied from 0.005-0.5 mg/ml. FIG. 2 shows a plot of the clotting times (in seconds) with increasing concentration of each different dendrimer.

The results show that dendrimer No. 5 (with only two fibrinogen-binding peptides/dendrimer) was not able to copolymerise with fibrinogen. As the number of fibrinogen-binding peptides was increased from three to five, at concentrations of dendrimer from ~0.125 to ~0.275 mg/ml, the speed of copolymerisation increased. At concentrations below ~0.125 mg/ml dendrimer, dendrimer No. 10 (with three fibrinogen-binding peptides/dendrimer) produced faster clotting times than dendrimer no. 4 (with four fibrinogen-binding peptides/dendrimer). In the range ~0.02-0.5 mg/ml, dendrimer no. 12 (with five fibrinogen-binding peptides/dendrimer) produced almost instantaneous clotting. In the range ~0.05-0.3 mg/ml, dendrimer no. 11 (with four fibrinogen-binding peptides/dendrimer) also produced almost instantaneous clotting.

It is concluded that the speed at which fibrinogen is polymerised by a dendrimer generally increases as the number of fibrinogen-binding peptides per dendrimer is increased.

EXAMPLE 4

Effect of Fibrinogen-Binding Peptide Orientation, and of Different Fibrinogen-Binding Peptide Sequences on Speed of Copolymerisation with Fibrinogen To assess whether the orientation of a fibrinogen-binding peptide could affect the ability of a peptide dendrimer to copolymerise with fibrinogen, peptide dendrimers comprising three fibrinogen-binding peptides attached to a single tri-functional amino acid residue (lysine) were synthesised (referred to as 'three-branch' dendrimers), but with one of the fibrinogen-binding peptides orientated with its amino-terminal end attached to the branched core, and amidated at its carboxy-terminal end. The ability of peptide dendrimers comprising different fibrinogen-binding peptide sequences to copolymerise with fibrinogen was also tested.

The fibrinogen-binding peptides of Peptide Dendrimer Nos. 3 and 10 are each of sequence GPRPG (SEQ ID NO: 17). Each fibrinogen-binding peptide of Peptide Dendrimer No. 10 is orientated with its carboxy-terminal end attached to the branched core. One of the fibrinogen-binding peptides of Peptide Dendrimer No. 3 is orientated with its amino-terminal end attached to the branched core. The carboxy-terminal end of that peptide comprises an amide group.

Two of the fibrinogen-binding peptides of Peptide Dendrimer No. 8 are of sequence GPRPG (SEQ ID NO: 17), and the third fibrinogen-binding peptide is of sequence APFPRPG (SEQ ID NO: 14) orientated with its amino-terminal end attached to the branched core. The carboxy-terminal end of that peptide comprises an amide group.

Two of the fibrinogen-binding peptides of Peptide Dendrimer No. 9 are of sequence GPRPFPA (SEQ ID NO: 3), and the third fibrinogen-binding peptide is of sequence APFPRPG (SEQ ID NO: 14) orientated with its amino-terminal end attached to the branched core. The carboxy-terminal end of that peptide comprises an amide group.

The sequence GPRPG (SEQ ID NO: 17) binds to hole 'a' and hole 'b' of fibrinogen, but with some preference for hole 'a'. The sequence GPRPFPA (SEQ ID NO: 3) binds with high preference for hole 'a' in fibrinogen. The sequence Pro-Phe-Pro stabilizes the backbone of the peptide chain and enhances the affinity of the knob-hole interaction (Stabenfeld et al., BLOOD, 2010, 116: 1352-1359).

Figure 3:
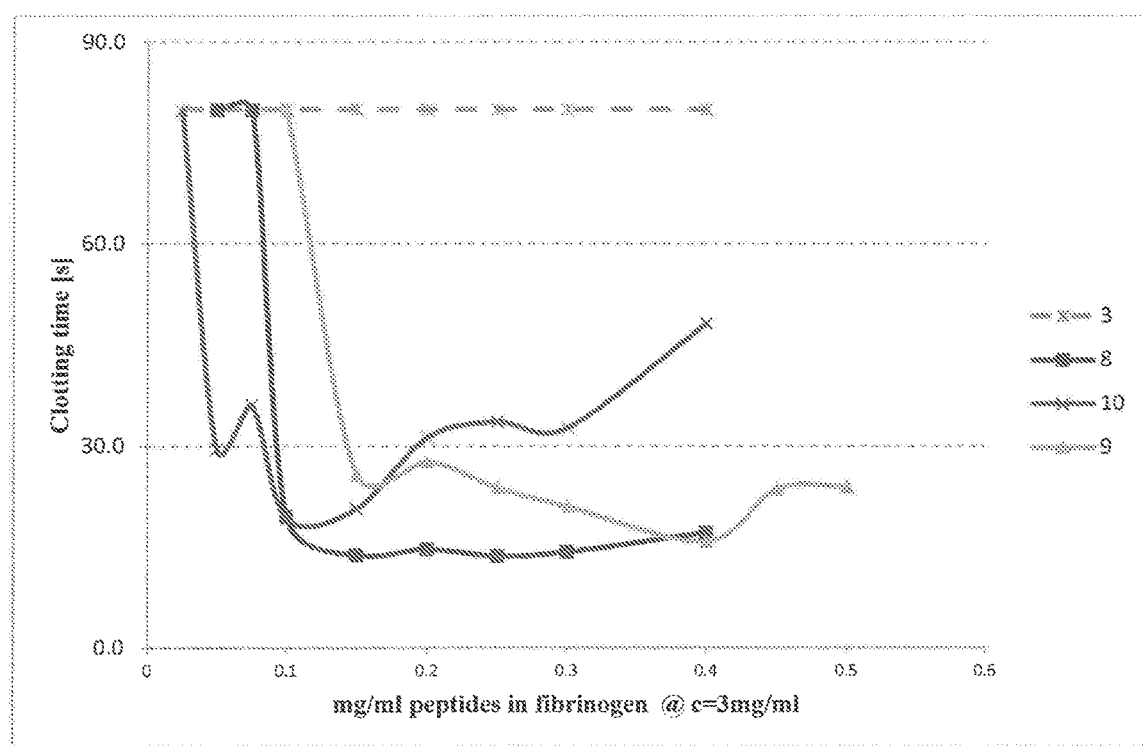
FIG. 3 shows the ability of several different peptide dendrimers to polymerise fibrinogen at varying concentrations. The numbering refers to the identity of the peptide dendrimer.

The ability of the dendrimers to copolymerise with fibrinogen was assessed using the same method described in Example 2, for a concentration of each dendrimer ranging from 0.005-0.5 mg/ml. FIG. 3 shows a plot of the clotting times (in seconds) obtained with increasing concentration of each different dendrimer.

The results show that changing the orientation of one of the fibrinogen-binding peptides of a three-branch dendrimer, so that the peptide is orientated with its amino-terminal end attached to the branched core (i.e. Dendrimer No. 3), reduced the ability of the dendrimer to copolymerise with fibrinogen (compare the clotting time of Dendrimer No. 3 with that of Dendrimer No. 10). However, at higher fibrinogen concentrations, Dendrimer No. 3 was able to copolymerise with fibrinogen (data not shown).

A three-branch dendrimer with a fibrinogen-binding peptide of different sequence orientated with its amino-terminal end attached to the branched core was able to copolymerise with fibrinogen (see the results for Dendrimer No. 8).

A three-branch dendrimer in which two of the fibrinogen-binding peptides comprise sequence that binds preferentially to hole 'b' in fibrinogen (sequence GPRPFPA (SEQ ID NO: 3)), with these peptides orientated with their carboxy-terminal end attached to the branched core, and the other peptide comprising the reverse sequence (i.e. sequence APFPRPG (SEQ ID NO: 14)) orientated with its amino-terminal end attached to the branched core (Dendrimer No. 9) was also very active in copolymerising with fibrinogen.

EXAMPLE 5

Ability of Peptide Dendrimers with Different Fibrinogen-Binding Peptide Sequences to Copolymerise with Fibrinogen The GPRPG (SEQ ID NO: 15) and GPRPFPA (SEQ ID NO: 3) motifs primarily bind to the 'a' hole on fibrinogen. This example describes an assessment of the ability of a chimeric peptide dendrimer (i.e. a peptide dendrimer with different fibrinogen-binding peptide sequences attached to the same branched core) to copolymerise with fibrinogen.

Peptide dendrimer No. 13 is a chimeric four-branch peptide dendrimer comprising two fibrinogen-binding peptides with sequence GPRPG- (SEQ ID NO: 17) (which has a binding preference for the 'a' hole), and two fibrinogen-binding peptides with sequence GHRPY- (SEQ ID NO: 11) (which binds preferentially to the 'b' hole). Non-chimeric peptide dendrimers Nos. 11 and 12 are four- and five-arm peptide dendrimers, respectively. Each fibrinogen-binding peptide of these dendrimers has the sequence GPRPG- (SEQ ID NO: 17). Each fibrinogen-binding peptide of Dendrimers Nos. 11, 12, and 13 is attached at its carboxy-terminal end to the branched core.

Figure 4:
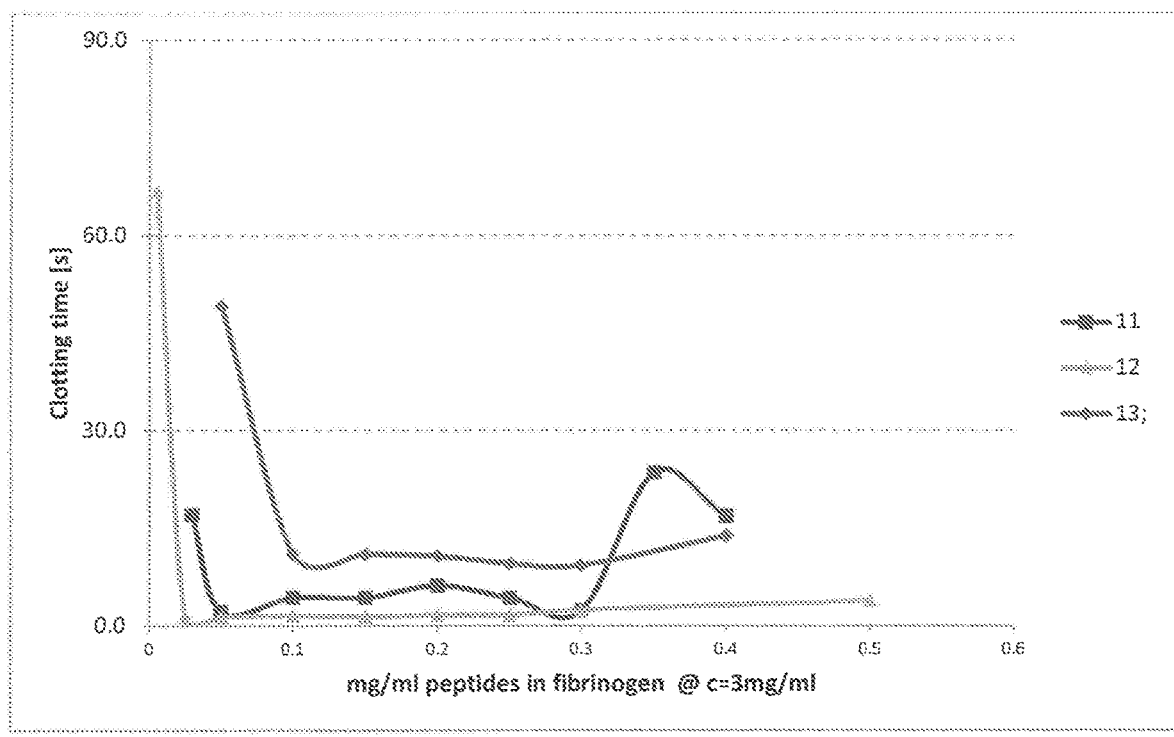
FIG. 4 shows the ability of several different peptide dendrimers to polymerise fibrinogen at varying concentrations. The numbering refers to the identity of the peptide dendrimer.

The ability of the dendrimers to copolymerise with fibrinogen was assessed using the same method described in Example 2, for a concentration of each dendrimer ranging from 0.005-0.5 mg/ml. FIG. 4 shows a plot of the clotting times (in seconds) obtained with increasing concentration of each different dendrimer.

Figure 5:
FIG. 5 shows a photograph of hydrogels formed by polymerisation of fibrinogen using different peptide dendrimers.

The results show that the clotting speed using the chimeric dendrimer was slower than the non-chimeric dendrimers at concentrations below 0.3 mg/ml. However, FIG. 5 shows a photograph of the hydrogels obtained using the different dendrimers. The gels are labelled with the number of the peptide dendrimer used (11, 12, and 13), and "P" labels a hydrogel formed using a product in which several fibrinogen-binding peptides are attached to soluble human serum albumin. The hydrogel formed by the chimeric dendrimer was more dense and contained less fluid compared to the hydrogels formed using dendrimers Nos. 11 and 12 (at 3 mg/ml fibrinogen, or at higher concentrations of fibrinogen). Thus, although the clotting time was slower using the chimeric dendrimer, the hydrogel formed using this dendrimer was more dense.

EXAMPLE 6

Ability of Mixtures of Peptide Dendrimers and Peptide Conjugates to Copolymerise with Fibrinogen Fibrinogen-binding peptide of sequence GPRP- (SEQ ID NO: 1) binds strongly and preferentially to the 'a' hole of fibrinogen (Laudano et al., 1978 PNAS 7S). Peptide Conjugate No. 1 comprises two fibrinogen-binding peptides with this sequence, each attached to a lysine residue. The first peptide is attached its carboxy-terminal end by a linker to the lysine residue, and the second peptide is attached at its amino-terminal end by a linker to the lysine residue. The carboxy-terminal end of the second peptide comprises an amide group.

Fibrinogen-binding peptide of sequence GHRPY- (SEQ ID NO: 11) binds strongly and preferentially to the 'b' hole of fibrinogen (Doolittle and Pandi, Biochemistry 2006, 45, 2657-2667). Peptide Conjugate No. 2 comprises a first fibrinogen-binding peptide with this sequence, attached at its carboxy-terminal end by a linker to a lysine residue. A second fibrinogen-binding peptide, which has the reverse sequence (YPRHG (SEQ ID NO: 16)), is attached at its amino terminal end by a linker to the lysine residue. The carboxy-terminal end of the second peptide comprises an amide group.

The linker allows the peptides to extend away from each other.

Figure 6:
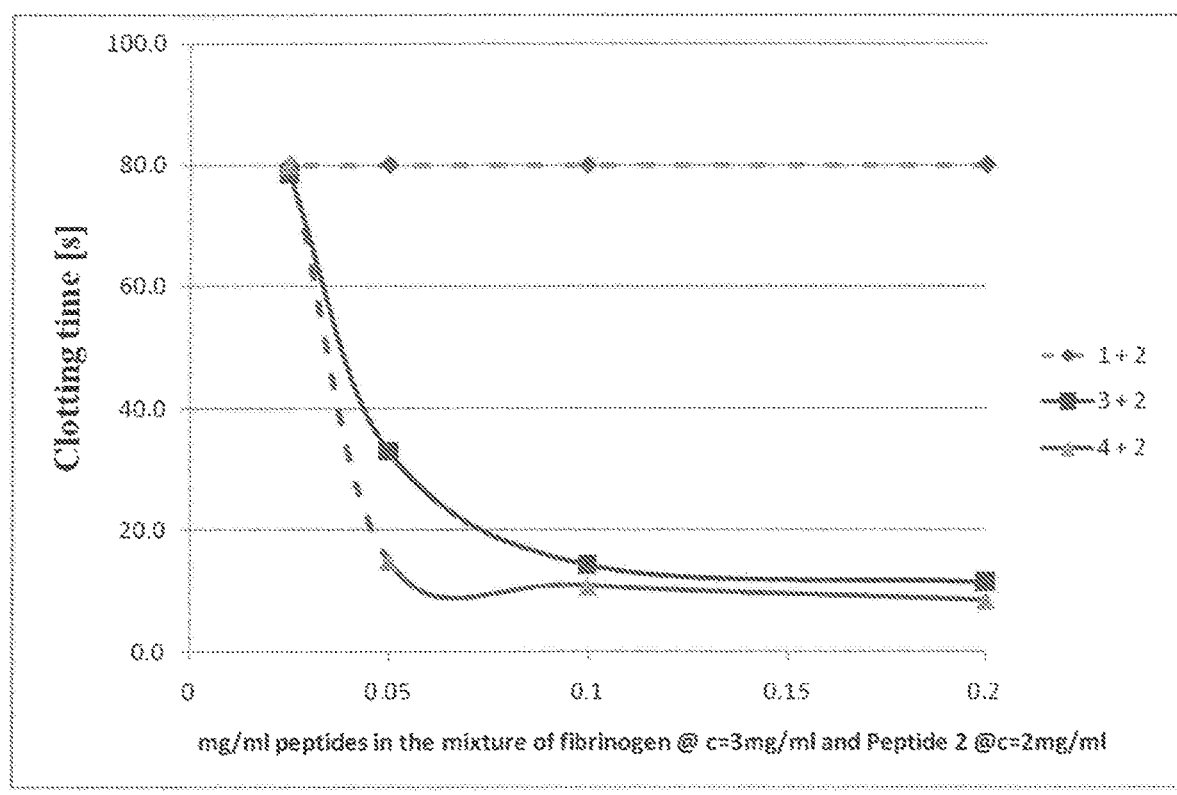
FIG. 6 shows the ability of different combinations of peptide dendrimers with peptide conjugates to polymerise fibrinogen at varying concentrations.

Peptide Conjugate No. 1 or 2 (2 mg/ml) was mixed with Peptide Dendrimer No. 3 or 4, and fibrinogen, and the ability of the mixtures to copolymerise with fibrinogen was assessed using the same method described in Example 2, for a concentration of each dendrimer ranging from 0.025-0.5 mg/ml. FIG. 6 shows a plot of the clotting times (in seconds) obtained with increasing concentration of each different dendrimer.

The results show that, surprisingly, only mixtures containing Peptide Conjugate No. 2 (i.e. with the B-knob peptides) and the dendrimer peptides were synergistic and increased activity, whereas mixtures containing the Peptide Conjugate No. 1 (the A-knob peptides) were not active when added to either Peptide Conjugate No. 2 or the peptide dendrimers.

EXAMPLE 7

Ability of Peptide Dendrimers to Polymerise Fibrinogen in Human Plasma

The ability of several different peptide dendrimers (Nos. 4, 5, 8, 9, 10, 11, 12, 13) to polymerise fibrinogen in human plasma was tested.

30 µL of each dendrimer (at a concentration of 0.25 mg/ml) was added to 100 µL human plasma at 37° C., and polymerisation of fibrinogen was determined using a Sigma Amelung KC4 Delta coagulation analyzer.

Figure 7:
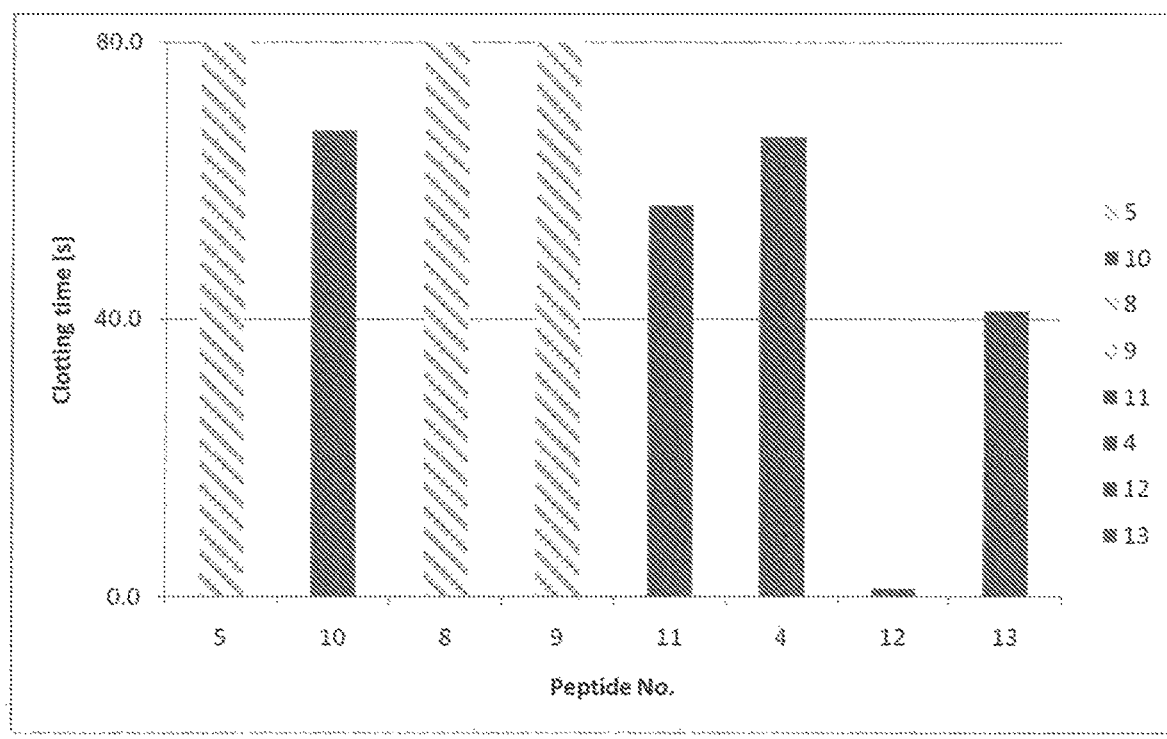
FIG. 7 shows the ability of several different peptide dendrimers to polymerise fibrinogen in human plasma.

The clotting times for each dendrimer are shown in FIG. 7, and show that peptide dendrimers Nos. 10, 11, 4, 12 and 13 were able to polymerise fibrinogen in human plasma, with dendrimer No. 12 being particularly effective (with a clotting time of less than one second). However, peptide dendrimers Nos. 5, 8, and 9 were not able to polymerise fibrinogen in human plasma.

EXAMPLE 8

Effect of Steam Sterilisation on a Haemostatic Agent in Solution

This example describes the effect of steam sterilisation on the haemostatic activity of a haemostatic agent (Peptide Dendrimer No. 12 (see Example 1): "HXP12") formulated in saline.

HXP12 at a concentration of 50 mg/ml was diluted with 150 mM sodium chloride to a concentration of 0.5 mg/ml. The formulation was prepared as a 6 ml bulk solution (using 60 µl of HXP12 stock). 400 µl of this bulk solution was used for each 2 ml glass vial, with a screw-fit air-tight lid. Each vial was autoclaved (200 kPa) for 25 minutes at 121° C. After sterilisation, the vials were placed at 40° C. and stored for up to 27 weeks.

To test the ability of the stored samples to polymerise fibrinogen, each sample was diluted with 20 mM phosphate buffer, pH 7.6, to a concentration of 0.05 mg/ml. 30 µl of each diluted sample was added to 100 µl of human fibrinogen, at a concentration of 3 mg/ml, formulated in 20 mM phosphate buffer, pH 7.6. The ability of HXP12 in each diluted sample to polymerise fibrinogen (the 'clotting' activity) at 37° C. was determined using a Sigma Amelung KC4 Delta coagulation analyser. The polymerisation activity of non-sterilised, control samples was also determined. The results are summarized in Table 1 below.

TABLE 1

| | | | Clotting activity (seconds) in human fibrinogen | | | |
|---|---|---|---|---|---|---|
| | Non autoclaved | Autoclaved @ 121° C. | After sterilization storage @ 40° C. | | | |
| | | | 4 wks | 7 wks | 13 wks | 27 wks |
| HXP12 c = 0.05 mg/ml | 1.1 | 1.0 | 0.9 | 1.2 | 1.1 | 1.1 |

The results in Table 1 show that the haemostatic agent formulated in saline retains its ability to polymerise fibrinogen after sterilization by steam in an autoclave (200 kPa) for 25 minutes at 121° C., and that this activity is retained even after storage at 40° C. for at least 27 weeks.

EXAMPLE 9

Effect of Steam Sterilisation on a Ready-to-Use, Flowable, Haemostatic Composition This example describes the effect of steam sterilisation on the haemostatic activity of a haemostatic agent (HXP12) formulated as a ready-to-use, flowable paste comprising Hyaluronic Acid (HA) cross-linked particles.

0.6 ml of a solution of HXP12 dissolved in water was mixed with 1.4 g of HA hydrogel particles hydrated in 10 mM phosphate buffer (HA concentration 2.7%; cross-linking 5:1 [HA/divinyl sulfone "DVS"], fully hydrated particle size 400 µm) to form a paste in which the concentration of HXP12 was 1 mg/ml. 200 mg of the paste was aliquoted into to glass vials, and each vial was closed with a lid. The vials were autoclaved (200 kPa) for 25 min at 121° C. After sterilisation, vials were placed at 80° C. for an extra 16 hours to simulate an accelerated aging process. The samples were assessed at 4 and 16 hours.

HXP12 was extracted from the stored samples, and diluted with 20 mM phosphate buffer, pH 7.2, to a concentration of 0.1 mg/ml. 30 µl of each extracted sample was added to 100 µl of human plasma (Alpha Labs), and the ability of HXP12 in each diluted sample to polymerise fibrinogen (the 'clotting' activity) at 37° C. was determined using a Sigma Amelung KC4 Delta coagulation analyser. The polymerisation activity of non-sterilised, control samples was also determined. The results are summarized in Table 2 below.

TABLE 2

| | Clotting activity (seconds) in human plasma | | | |
|---|---|---|---|---|
| | Non autoclaved | Autoclaved @ 121° C. | After sterilization, accelerated aging study @ 80° C. | |
| | | | 4 hours | 16 hours |
| Extracted HXP12 c = 0.1 mg/ml | 2.0 | 2.6 | 2.8 | 4.8 |

The results in Table 2 show that HXP12 peptide, formulated as a ready-to-use, flowable paste with HA hydrogel particles, retains ability to polymerise fibrinogen from human plasma after sterilization by steam in an autoclave (200 kPa) for 25 minutes at 121° C., and that this activity is retained even after storage at 80° C. for at least 4 hours.

EXAMPLE 10

Effect of Steam Sterilisation on a Ready-to-Use, Flowable, Haemostatic Composition This example describes the effect of steam sterilisation on the haemostatic activity of a haemostatic agent (HXP12) formulated as a ready-to-use, flowable paste made of Hyaluronic Acid (HA) cross-linked particles.

0.6 ml of a solution of HXP12 formulated in 10 mM phosphate buffer, 160 mM Arg.HCl, pH 6.8, was mixed with 1.4 g of HA hydrogel particles (HA concentration 2.7%; cross-linking 5:1 [HA/divinyl sulfone "DVS"], fully hydrated particle size 400 µm) to form a paste in which the concentration of HXP12 was 1 mg/ml. 200 mg of the paste was aliquoted into glass vials, and each vial was closed with a lid. The vials were autoclaved (200 kPa) for 25 min at 121° C. After sterilisation, vials were placed at 40° C. The samples were assessed at 0, 2 and 4 weeks.

HXP12 was extracted from the stored samples, and diluted with 20 mM phosphate buffer, pH 7.2, to a concentration of 0.06 mg/ml. 30 µl of each extracted sample was added to 100 µl of human fibrinogen at a concentration of 3 mg/ml (the level of fibrinogen found in the blood) formulated in 20 mM phosphate buffer, pH 7.2. The ability of HXP12 in each diluted sample to polymerise fibrinogen (the 'clotting' activity) at 37° C. was determined using a Sigma Amelung KC4 Delta coagulation analyser. The polymerisation activity of non-sterilised, control samples was also determined. The results are summarized in Table 3 below.

TABLE 3

| | Clotting activity (seconds) in human fibrinogen @ c = 3 mg/ml | | | |
|---|---|---|---|---|
| | | | After sterilization, accelerated aging study @ 40° C. | |
| Extracted HXP12 | Non autoclaved | Autoclaved @ 121° C. | 2 weeks | 4 weeks |
| c = 0.06 mg/ml | 1.0 | 3.3 | 3.6 | 5.4 |

The results in Table 3 show that HXP12 peptide, formulated as a ready-to-use, flowable paste with HA hydrogel particles, retains ability to polymerise fibrinogen from human fibrinogen after sterilization in an autoclave for 25 minutes at 121° C. (200 kPa), and that this activity is retained even after storage at 40° C. for at least 2 weeks.

EXAMPLE 11

Assessment of the Haemostatic Activity of a Haemostatic Composition of the Invention in a Rabbit Liver Biopsy Injury Model This example describes testing of the haemostatic activity of three different compositions of the invention, each with a different concentration of a haemostatic agent (HXP12 peptide dendrimer).

Methods 7 g of HA paste (HA concentration 2.7%; 5:1; HA/DVS, fully hydrated particle size 400 µm) was prefilled into a syringe and mixed with 3 ml of HXP12 peptide dendrimer at one of three different concentrations, resulting in 10 ml of the final product. The final HXP12 concentration for each 10 ml product was: sample B, 1 mg/ml; B2, 0.5 mg/ml; B3, 1.4 mg/ml. As a control (C), 7 g of HA paste was mixed with 3 ml of saline.

Figure 8:
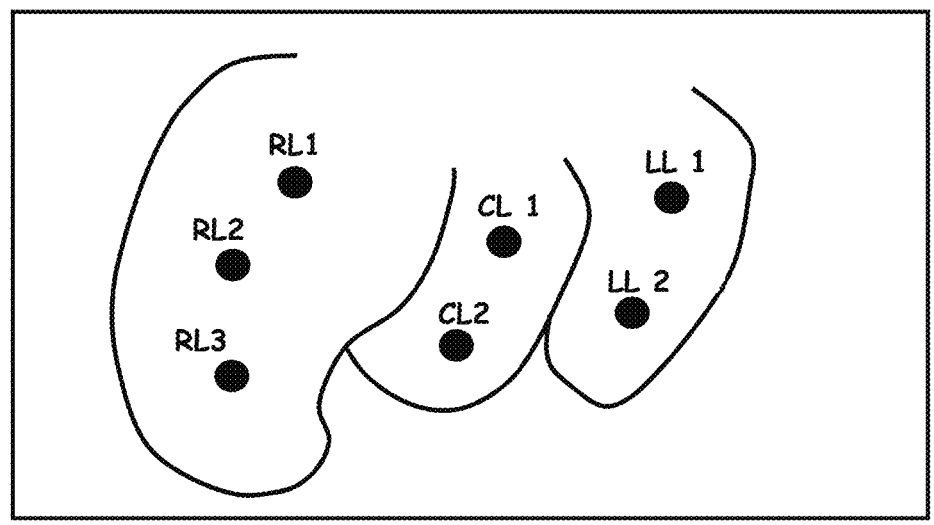
FIG. 8A shows a schematic drawing of rabbit liver lobes indicating the approximate position of liver biopsy injuries.
FIG. 8B illustrates how the degree of bleeding was assessed on a scale of 0 to 5.
Figure 8:
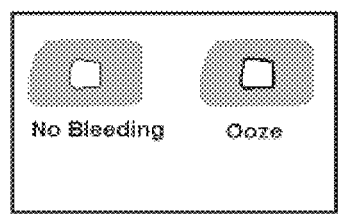

Heparinised rabbits (Breed: New Zealand White; Sex: Males) were anaesthetized. All three lobes of the liver were withdrawn from the abdominal cavity and laid on saline-wet gauze swabs. Samples were tested on biopsy injuries which were created sequentially on the three liver lobes as set out below in Table 3. FIG. 8A shows the approximate orientation and order of liver injury on the three lobes.

TABLE 4

Order and location of injury to liver lobes

| | Cut No: | | | | | | |
|---|---|---|---|---|---|---|---|
| | 1 | 2 | 3 | 4 | 5 | 6 | 7 |
| Lobe: | Left | Left | Central | Central | Right | Right | Right |
| Cut name: | LL1 | LL2 | CL1 | CL2 | RL1 | RL2 | RL3 |

Biopsies were created on the lobes of the liver using a 6 mm biopsy punch to approximately 5 mm depth. A pre-weighed dry swab was used to collect blood exiting the wound for 15 seconds. The swab was then weighed as a measure of bleeding severity. After removal of the swab, the wound was dried with another swab and then the test samples applied.

For the application of tested samples, a saline-moistened sterile gauze swab was applied against the bleeding surface, and the syringe was used to dispense up to 2 ml of Sample B, B2, or B3, or 2 ml of the control (C), between the gauze and the bleeding surface into the biopsy wound. Gentle pressure was applied to the gauze swab for one minute after application. Upon removal of the moist gauze, the wound was evaluated for haemostasis at 1, 3, 6, 9 and 12 min after the application of the test sample (i.e. including one minute application of pressure).

Bleeding scores of 0, 1, 2, 3, 4 and 5 were assigned for no bleeding, oozing, very mild, mild, moderate, and severe bleeding, respectively (FIG. 8B). The scores for the degree of bleeding were adapted from Adams et al (J Thromb Thrombolysis DOI 10.1007/s 11239-008-0249-3). On successful haemostasis, the lobe was covered with a saline soaked swab and the procedure repeated until each lobe had received treatment as described above.

Results

FIG. 9 is a photograph of one of the biopsied livers. Blood can be seen flowing from a biopsy site treated with the control (shown above the label "Control"), whereas the haemostatic effect at a biopsy site treated with a composition of the invention comprising HA paste and HXP12 (shown above the label "HA paste+HXP12") is clearly visible.

FIG. 10 shows a plot of the haemostatic effect (% haemostatic success) of samples B, B2, and B3, compared with the control, over the time (in minutes) of the evaluation. In contrast to the control, each of the different compositions comprising HA paste and HXP12 peptide dendrimer demonstrated strong coagulant activity. This activity was dose-dependent, with the compositions having higher concentrations of HXP12 (samples B and B3) demonstrating approximately 80%-100% haemostatic activity throughout the 12-minute evaluation. The composition with the lowest concentration of HXP12 (sample B2) demonstrated 100% haemostatic activity for the first three minutes of the evaluation, but this then reduced to ~75% over the remaining 9 minutes.

This example shows that an embodiment of a composition of the invention comprising HA particles that are essentially not haemostatic, and a peptide dendrimer that has coagulant properties, is surprisingly effective in controlling bleeding.

EXAMPLE 12

A Sterile, Ready-to-Use, Flowable Haemostatic Composition Comprising Cross-Linked HA Gel Particles, and a Haemostatic Agent A flowable paste made from cross-linked hyaluronic acid (HA) gel particles (HA concentration 2.7%; 5:1; HA/DVS, fully hydrated particle size 400 µm) was made transparent by centrifuging the paste at 600 rpm for 5 minutes. The transparent paste is shown in FIG. 11A.

7 g of the transparent HA paste was mixed with 3 ml of HXP12 peptide dendrimer (formulated in 10 mM phosphate buffer, 160 mM Arg.HCl, pH 6.8) resulting in 10 ml of the final product. The final concentration of HXP12 was 1.05 mg/ml. FIG. 11B shows a photograph of some of the resulting composition. The photograph shows that the composition is sufficiently cohesive to form a continuous layer over a wound, and thus can be used to seal a wound.

The composition was placed in a glass vial, and sterilised by steam sterilisation in an autoclave (200 kPa) for 25 minutes at 121° C.

FIG. 11C shows a photograph of a syringe containing the composition. FIG. 11D shows a syringe containing the composition, in which some of the composition has been extruded though the opening at the tip of the syringe barrel using its plunger.

FIG. 11E shows a photograph of an embodiment of a transparent composition of the invention that has been deposited over surgical suture material of size code "0", diameter 0.3-0.39 mm. The suture material is clearly visible through the transparent composition.

A surgeon can see through a transparent composition of the invention when administering it. This makes it much easier to administer the composition correctly, and determine whether it has been effective in controlling or stopping bleeding.

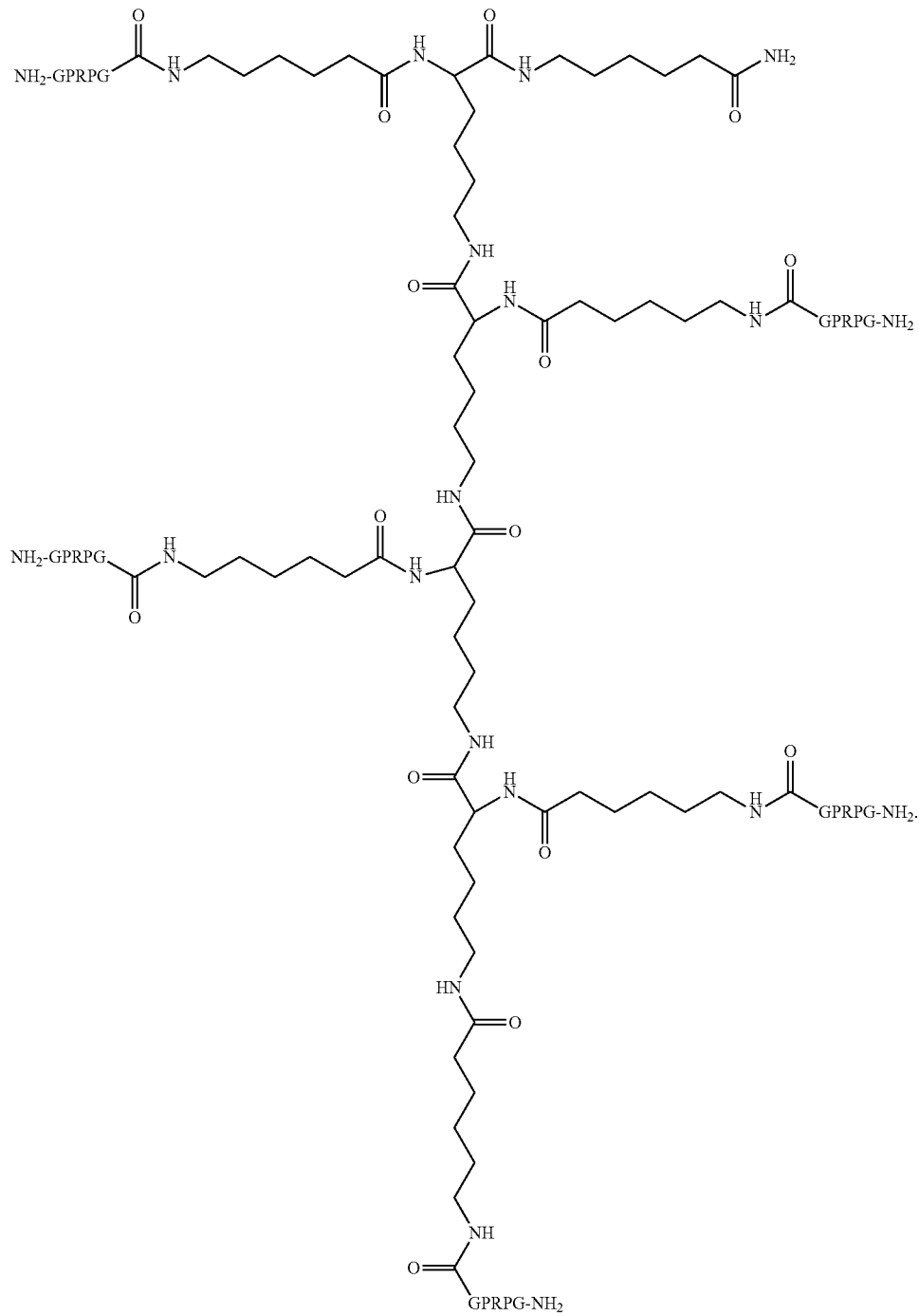

The invention claimed is:

1. A sterile, ready-to-use, flowable haemostatic composition comprising:
a soluble haemostatic agent having the following general formula (I):

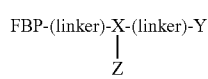
(I)

where:
FBP is a fibrinogen-binding peptide;
-(linker)- is non-peptide linker comprising —NH(CH$_2$)$_n$CO—, where n is 1-10;
X is a tri-functional amino acid residue;
Y is —FBP or —NH$_2$; and
Z is -[—X-(linker)-FBP]$_a$-(linker)-FBP, where a is 1-10;
a biocompatible liquid; and
particles of a biocompatible cross-linked polysaccharide suitable for use in haemostasis and which are insoluble in the biocompatible liquid.

2. The composition according to claim 1, wherein the haemostatic composition has been sterilized by steam sterilization, or by dry-heat sterilization.

3. The composition according to claim 1, wherein the biocompatible liquid provides a continuous liquid phase, and the polymer particles are substantially homogenously dispersed throughout the liquid phase.

4. The composition according to claim 1, wherein the tri-functional amino acid residues of Formula (I) comprise a lysine, ornithine, arginine, aspartic acid, glutamic acid, asparagine, glutamine, or cysteine residue.

5. The composition according to claim 1, wherein the haemostatic agent is of the following general formula (II):

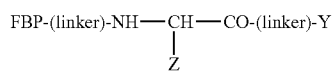
(II)

where:
FBP is a fibrinogen-binding peptide;
-(linker)- is a non-peptide linker comprising —NH(CH$_2$)$_n$CO— wherein n is 1-10;
Y is —FBP, or —NH$_2$;
Z is:
—R-(linker)-FBP, when Y is —FBP, or

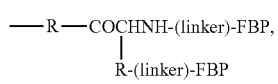

when Y is —NH$_2$; or

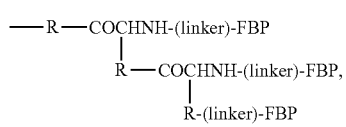

when Y is —NH$_2$; or

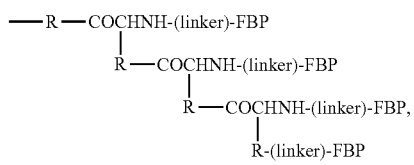

when Y is —NH$_2$; or

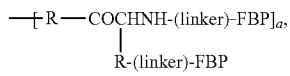

when Y is —FBP and a is 1-10
where R is —(CH$_2$)$_4$NH—, —(CH$_2$)$_3$NH—, or —(CH$_2$)$_3$NHCNHNH.

6. The composition according to claim 1, wherein the haemostatic agent is of the following general formula (III):

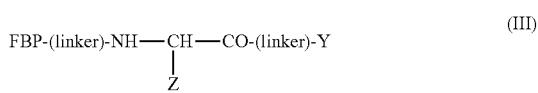
(III)

where:
FBP is a fibrinogen-binding peptide;
-(linker)- is a non-peptide linker comprising —NH(CH$_2$)$_n$CO— wherein n is 1-10;
Y is —FBP, or —NH$_2$;
Z is:
—(CH$_2$)$_4$NH-(linker)-FBP, when Y is —FBP; or

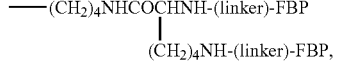

when Y is —NH$_2$; or

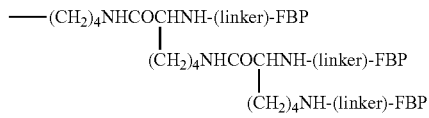

when Y is —NH$_2$; or

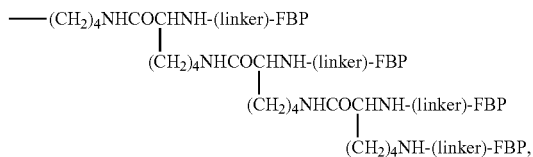

when Y is —NH$_2$; or

when Y is —FBP and a is 1-10.

7. The composition according to claim 1, wherein the fibrinogen-binding peptides bind preferentially to hole 'a' of fibrinogen over hole 'b' of fibrinogen.

8. The composition according to claim 1, wherein the biocompatible liquid is an aqueous solution.

9. The composition according to claim 8, wherein the aqueous solution is a saline solution.

10. The composition according to claim 1, wherein the polysaccharide comprises a glycosaminoglycan, oxidized cellulose, chitosan, chitin, alginate, oxidized alginate, or oxidized starch.

11. The composition according to claim 10, wherein the glycosaminoglycan comprises hyaluronic acid.

12. The composition according to claim 1, wherein the particles comprise cross-linked hyaluronic acid granules, wherein a majority of the granules have a diameter in the range 100-1500 μm in partially or fully hydrated form.

13. The composition according to claim 1, having a solids content of 1-70%, or 5-20%, by weight of the composition.

14. The composition according to claim 1, wherein a weight ratio of the particles to the liquid is from 1:1 to 1:12, or from 1:3 to 1:8.

15. The composition according to claim 1, wherein the composition is transparent.

16. The composition according to claim 1, wherein the tri-functional amino acid residues of Formula (I) are lysine residues.

17. The composition according to claim 1, wherein the soluble haemostatic agent has the following structure: